US008398987B2

(12) United States Patent
Urbaniak et al.

(10) Patent No.: US 8,398,987 B2
(45) Date of Patent: Mar. 19, 2013

(54) USE OF PLATELET GLYCOPEPTIDE IIIA EPITOPES IN THE TREATMENT OF IMMUNE THROMBOCYTOPENIC PURPURA

(75) Inventors: Stanislaw Joseph Urbaniak, Aberdeen (GB); Robert Norman Barker, Inverurle (GB); Hosea Sukati, Aberdeen (GB)

(73) Assignees: The University Court of the University of Aberdeen, Aberdeen (GB); The Common Services Agency for the Scottish Health Service, Edinburgh (GB)

( * ) Notice: Subject to any disclaimer, the term of this patent is extended or adjusted under 35 U.S.C. 154(b) by 123 days.

(21) Appl. No.: 12/523,549

(22) PCT Filed: Jan. 18, 2008

(86) PCT No.: PCT/EP2008/050595
§ 371 (c)(1),
(2), (4) Date: Dec. 7, 2009

(87) PCT Pub. No.: WO2008/087216
PCT Pub. Date: Jul. 24, 2008

(65) Prior Publication Data
US 2010/0086562 A1 Apr. 8, 2010

(30) Foreign Application Priority Data

Jan. 18, 2007 (GB) .................................. 0701048.1

(51) Int. Cl.
*A61K 39/00* (2006.01)
(52) U.S. Cl. .................. 424/185.1; 424/193.1; 424/810; 514/13.7; 514/14.9; 530/326
(58) Field of Classification Search .......................... None
See application file for complete search history.

(56) References Cited

U.S. PATENT DOCUMENTS 5,939,524 A * 8/1999 Bowditch et al. ............. 530/324

FOREIGN PATENT DOCUMENTS

| CN | 1243708 | 2/2000 |
|---|---|---|
| WO | WO 00/72882 | 12/2000 |
| WO | WO 2004/005890 | 1/2004 |
| WO | WO 2004/064863 | 8/2004 |
| WO | WO 2005002613 A1 * | 1/2005 |

OTHER PUBLICATIONS

Goodnow CC., Lancet. Jun. 30, 2001;357(9274):2115-21.*
Skyler, J.S., et al. Diabetes Care. 2005;28:1068-1076.*
Pozzilli, P., et al. Diabetol. 2000;43:1000-1004.*
Dong, V.M., et al. Ped. Transplant.. 1999;161:181-189.*
Bell, J.J. et al. J. Immunol. 2008;180:1508-1516.*
Kraus, T.A., and Mayer, L. Curr. Opin. Gastroenterol. 2005;21:692-696.*
Schroeder, R.A., et al. J. Surg. Sci. Res. 2003;111:109-119.*
Marketletter (Sep. 13, 1999).*
Ludvigsson et al. , N Engl J Med 2012; 366:433-442.*
Barker et al. "Identification of T-Cell Epitopes on the Rhesus Polypeptides in Autoimmune Hemolytic Anemia" Blood 1997 vol. 90(7): 2701-2715.
Beardsley et al. "The Disulfide-Rich Region of Platelet Glycoprotein (GP) IIIa Contains Hydrophilic Peptide Sequences that Bind Anti-GPIIIa Autoantibodies from Patients with Immune Thrombocytopenic Purpura (ITP)" Biophysical Chemistry 2003 vol. 105: 503-515.
Bessos et al. "An International Trial Demonstrates Suitability of a Newly Developed Whole-Blood ELISA Kit for Multicentre Platelet HPA-1 Phenotyping" Vox Sang 1999 vol. 77: 103-106.
Bowditch et al. "Characterization of Autoantigenic Epitopes on Platelet Glycoprotein IIb/IIIa Using Random Peptide Libraries" Blood 1996 vol. 88(12): 4579-4584.
Cairns et al. "The Fine Specificity and Cytokine Profile of T-Helper Cells Responsive to the α3 Chain of Type IV Collagen in Goodpasture's Disease" J Am Soc Nephrol 2003 vol. 14: 2801-2812.
Gevorkian et al. "Identification of Autoimmune Thrombocytopenic Purpura-Related Epitopes Using Phage-Display Peptide Library" Clinical Immunology and Immunopathology 1998 vol. 86(3): 305-309.
Jacobin et al. "Improving Selection of αIIbβ3-Binding Phage Antibodies with Increased Reactivity Derived from Immunized Donors" Clinical Immunology 2003 vol. 108: 199-210.
Kekomaki et al. "Localization of Human Platelet Autoantigens to the Cysteine-Rich Region of Glycoprotein IIIa" J. Clin. Invest. 1991 vol. 88:847-854.
Kosugi et al. "Platelet-Associated Anti-GPIIb-IIIa Autoantibodies in Chronic Immune Thrombocytopenic Purpura Recognizing Epitopes Close to the Ligand-Binding Site of Glycoprotein (GP) IIb" Blood 2001 vol. 98(6): 1819-1827.
Kuwana et al. "Immunodominant Epitopes on Glycoprotein IIb-IIIa Recognized by Autoreactive T Cells in Patients with Immune Thrombocytopenic Purpura" Blood 2001 vol. 98(1): 130-139.
Kuwana et al. "Suppression of Autoreactive T-Cell Response to Glycoprotein IIb/IIIa by Blockade of CD40/CD154 Interaction: Implications for Treatment of Immune Thrombocytopenic Purpura" Blood 2003 vol. 101(2): 621-623.
McMillan, R. "Autoantibodies and Autoantigens in Chronic Immune Thrombocytopenic Purpura" Seminars in Hematology 2000 vol. 37(3): 239-248.
Semple, J.W. "Immune Pathophysiology of Autoimmune Thrombocytopenic Purpura" Blood Reviews 2002 vol. 16:9-12.
Stott et al. "Identification of Alloreactive T-Cell Epitopes on the Rhesus D Protein" Blood 2000 vol. 96(13): 4011-4019.
Sturniolo et al. "Generation of Tissue-Specific and Promiscuous HLA Ligand Databases Using DNA Microarrays and Virtual HLA Class II Matrices" Nature Biotechnology 1999 vol. 17: 555-561.
Sukati et al. "Characterization of the Alloreactive Helper T-Cell Response to the Platelet Membrane Glycoprotein IIIa (Integrin-(β3) in Human Platelet Antigen-1a Alloimmunized Human Platelet Antigen-1b1b Women" Transfusion 2005 vol. 45: 1165-1177.
Sukati et al. "Mapping Helper T-Cell Epitopes on Platelet Membrane Glycoprotein IIIa in Chronic Autoimmune Thrombocytopenic Purpura" Blood 2007 vol. 109(10): 4528-4538.
Tomiyama, Y. and Kosugi, S. "Autoantigenic Epitopes on Platelet Glycoproteins" International Journal of Hematology 2005 vol. 81: 100-105.

(Continued)

*Primary Examiner* — Michael Szperka
(74) *Attorney, Agent, or Firm* — Licata & Tyrrell P.C.

(57) ABSTRACT

The present invention relates to a composition for treating diseases associated with autoantibodies specific for platelet proteins, in particular autoimmune thrombocytopenic purpura. The composition, comprising an epitope of a platelet protein, treats diseases by tolerization.

5 Claims, 7 Drawing Sheets

OTHER PUBLICATIONS

Figure 1:
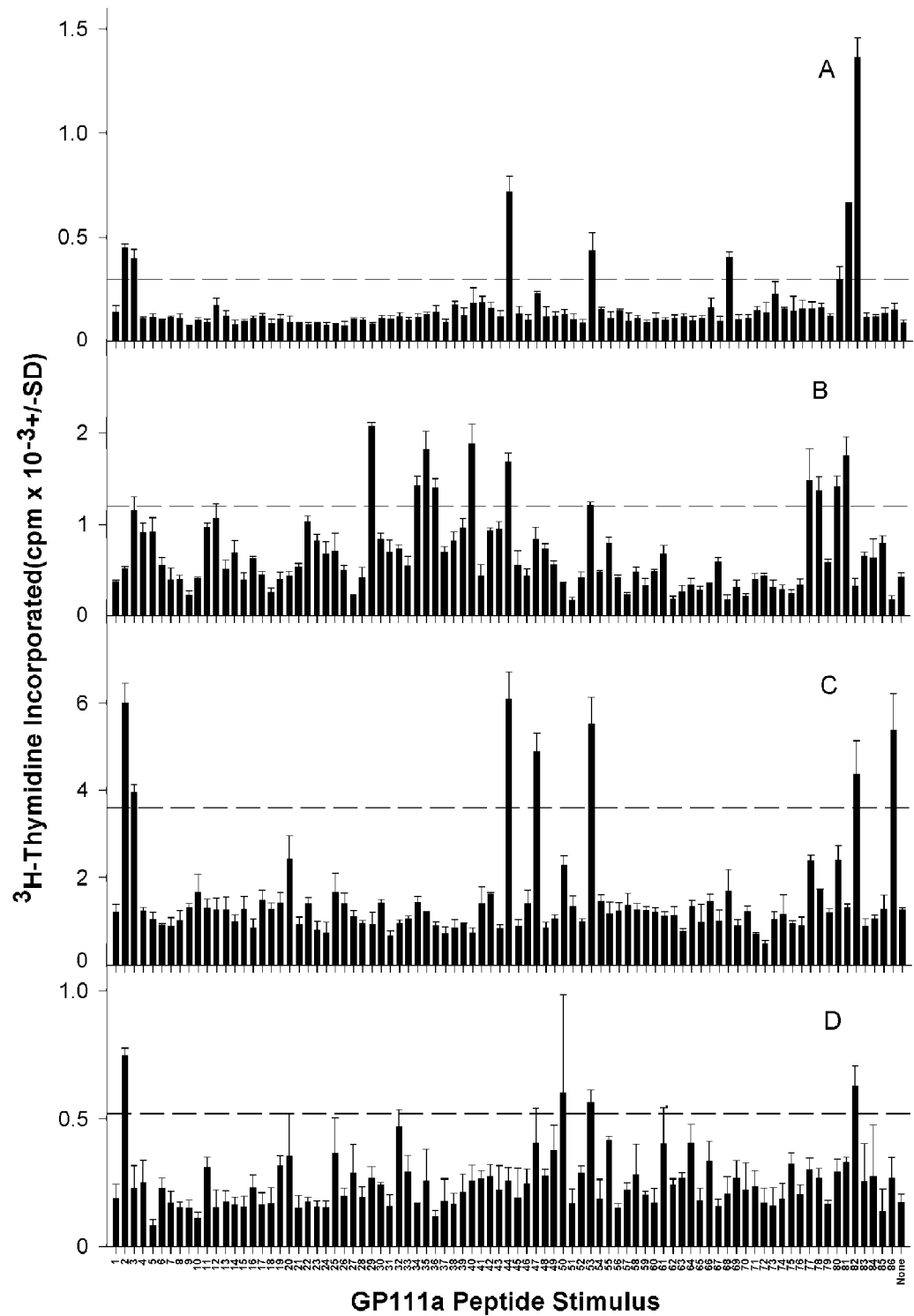

Campbell et al. "Peptide Immunotherapy in Allergic Asthma Generates IL-10-dependent Immunological Tolerance Associated with Linked Epitope Suppression" The Journal of Experimental Medicine 2009 206(7):1535-1547.

Kamphuis et al. "Tolerogenic Immune Responses to Novel T-cell Epitopes from Heat-shock Protein 60 in Juvenile Idiopathic Arthritis" The Lancet 2005 366:50-56.

Larché M. And Wraith, D. C. "Peptide-based Therapeutic Vaccines for Allergic and Autoimmune Diseases" Nature Medicine 2005 11(4):S69-S76.

Ludvigsson et al. "GAD Treatment and Insulin Secretion in Recent-onset Type 1 Diabetes" The New England Journal of Medicine 2008 359:1909-1920.

Newell et al. "Identification of a B Cell Signature Associated with Renal Transplant Tolerance in Humans" The Journal of Clinical Investigation 2010 120(6):1836-1847.

Thrower et al. "Proinsulin Peptide Immunotherapy in Type 1 Diabetes: Report of a First-in-man Phase I Safety Study" Clinical & Experimental Immunology 2008 155:156-165.

* cited by examiner

SEQUENCE LISTING

<160> NUMBER OF SEQ ID NOS: 86

<210> SEQ ID NO 1
<211> LENGTH: 15
<212> TYPE: PRT
<213> ORGANISM: Homo sapiens

<400> SEQUENCE: 1

Gly Pro Asn Ile Cys Thr Thr Arg Gly Val Ser Ser Cys Gln Gln
1               5                   10                  15

<210> SEQ ID NO 2
<211> LENGTH: 15
<212> TYPE: PRT
<213> ORGANISM: Homo sapiens

<400> SEQUENCE: 2

Thr Thr Arg Gly Val Ser Ser Cys Gln Gln Cys Leu Ala Val Ser

```
                1               5                  10                 15
```

<210> SEQ ID NO 3
<211> LENGTH: 15
<212> TYPE: PRT
<213> ORGANISM: Homo sapiens

<400> SEQUENCE: 3

```
Ser Ser Cys Gln Gln Cys Leu Ala Val Ser Pro Met Cys Ala Trp
1               5                   10                  15
```

<210> SEQ ID NO 4
<211> LENGTH: 15
<212> TYPE: PRT
<213> ORGANISM: Homo sapiens

<400> SEQUENCE: 4

```
Cys Leu Ala Val Ser Pro Met Cys Ala Trp Cys Ser Asp Glu Ala
1               5                   10                  15
```

<210> SEQ ID NO 5
<211> LENGTH: 15
<212> TYPE: PRT
<213> ORGANISM: Homo sapiens

<400> SEQUENCE: 5

```
Pro Met Cys Ala Trp Cys Ser Asp Glu Ala Leu Pro Leu Gly Ser
1               5                   10                  15
```

<210> SEQ ID NO 6
<211> LENGTH: 15
<212> TYPE: PRT
<213> ORGANISM: Homo sapiens

<400> SEQUENCE: 6

```
Cys Ser Asp Glu Ala Leu Pro Leu Gly Ser Pro Arg Cys Asp Leu
1               5                   10                  15
```

<210> SEQ ID NO 7
<211> LENGTH: 15
<212> TYPE: PRT
<213> ORGANISM: Homo sapiens

<400> SEQUENCE: 7

```
Leu Pro Leu Gly Ser Pro Arg Cys Asp Leu Lys Glu Asn Leu Leu
1               5                   10                  15
```

<210> SEQ ID NO 8
<211> LENGTH: 15
<212> TYPE: PRT
<213> ORGANISM: Homo sapiens

<400> SEQUENCE: 8

```
Pro Arg Cys Asp Leu Lys Glu Asn Leu Leu Lys Asp Asn Cys Ala
1               5                   10                  15
```

<210> SEQ ID NO 9
<211> LENGTH: 15
<212> TYPE: PRT
<213> ORGANISM: Homo sapiens

<400> SEQUENCE: 9

```
Lys Glu Asn Leu Leu Lys Asp Asn Cys Ala Pro Glu Ser Ile Glu
1               5                   10                  15
```

-continued

```
<210> SEQ ID NO 10
<211> LENGTH: 15
<212> TYPE: PRT
<213> ORGANISM: Homo sapiens

<400> SEQUENCE: 10

Lys Asp Asn Cys Ala Pro Glu Ser Ile Glu Phe Pro Val Ser Glu
1               5                   10                  15

<210> SEQ ID NO 11
<211> LENGTH: 15
<212> TYPE: PRT
<213> ORGANISM: Homo sapiens

<400> SEQUENCE: 11

Pro Glu Ser Ile Glu Phe Pro Val Ser Glu Ala Arg Val Leu Glu
1               5                   10                  15

<210> SEQ ID NO 12
<211> LENGTH: 15
<212> TYPE: PRT
<213> ORGANISM: Homo sapiens

<400> SEQUENCE: 12

Phe Pro Val Ser Glu Ala Arg Val Leu Glu Asp Arg Pro Leu Ser
1               5                   10                  15

<210> SEQ ID NO 13
<211> LENGTH: 15
<212> TYPE: PRT
<213> ORGANISM: Homo sapiens

<400> SEQUENCE: 13

Ala Arg Val Leu Glu Asp Arg Pro Leu Ser Asp Lys Gly Ser Gly
1               5                   10                  15

<210> SEQ ID NO 14
<211> LENGTH: 15
<212> TYPE: PRT
<213> ORGANISM: Homo sapiens

<400> SEQUENCE: 14

Asp Arg Pro Leu Ser Asp Lys Gly Ser Gly Asp Ser Ser Gln Val
1               5                   10                  15

<210> SEQ ID NO 15
<211> LENGTH: 15
<212> TYPE: PRT
<213> ORGANISM: Homo sapiens

<400> SEQUENCE: 15

Asp Lys Gly Ser Gly Asp Ser Ser Gln Val Thr Gln Val Ser Pro
1               5                   10                  15

<210> SEQ ID NO 16
<211> LENGTH: 15
<212> TYPE: PRT
<213> ORGANISM: Homo sapiens

<400> SEQUENCE: 16

Asp Ser Ser Gln Val Thr Gln Val Ser Pro Gln Arg Ile Ala Leu
1               5                   10                  15

<210> SEQ ID NO 17
<211> LENGTH: 15
<212> TYPE: PRT
```

<213> ORGANISM: Homo sapiens

<400> SEQUENCE: 17

Thr Gln Val Ser Pro Gln Arg Ile Ala Leu Arg Leu Arg Pro Asp
1               5                   10                  15

<210> SEQ ID NO 18
<211> LENGTH: 15
<212> TYPE: PRT
<213> ORGANISM: Homo sapiens

<400> SEQUENCE: 18

Gln Arg Ile Ala Leu Arg Leu Arg Pro Asp Asp Ser Lys Asn Phe
1               5                   10                  15

<210> SEQ ID NO 19
<211> LENGTH: 15
<212> TYPE: PRT
<213> ORGANISM: Homo sapiens

<400> SEQUENCE: 19

Arg Leu Arg Pro Asp Asp Ser Lys Asn Phe Ser Ile Gln Val Arg
1               5                   10                  15

<210> SEQ ID NO 20
<211> LENGTH: 15
<212> TYPE: PRT
<213> ORGANISM: Homo sapiens

<400> SEQUENCE: 20

Asp Ser Lys Asn Phe Ser Ile Gln Val Arg Gln Val Glu Asp Tyr
1               5                   10                  15

<210> SEQ ID NO 21
<211> LENGTH: 15
<212> TYPE: PRT
<213> ORGANISM: Homo sapiens

<400> SEQUENCE: 21

Ser Ile Gln Val Arg Gln Val Glu Asp Tyr Pro Val Asp Ile Tyr
1               5                   10                  15

<210> SEQ ID NO 22
<211> LENGTH: 15
<212> TYPE: PRT
<213> ORGANISM: Homo sapiens

<400> SEQUENCE: 22

Pro Val Asp Ile Tyr Tyr Leu Met Asp Leu Ser Tyr Ser Met Lys
1               5                   10                  15

<210> SEQ ID NO 23
<211> LENGTH: 15
<212> TYPE: PRT
<213> ORGANISM: Homo sapiens

<400> SEQUENCE: 23

Ser Tyr Ser Met Lys Asp Asp Leu Trp Ser Ile Gln Asn Leu Gly
1               5                   10                  15

<210> SEQ ID NO 24
<211> LENGTH: 15
<212> TYPE: PRT
<213> ORGANISM: Homo sapiens

<400> SEQUENCE: 24

```
Ile Gln Asn Leu Gly Thr Lys Leu Ala Thr Gln Met Arg Lys Leu
1               5                   10                  15
```

<210> SEQ ID NO 25
<211> LENGTH: 15
<212> TYPE: PRT
<213> ORGANISM: Homo sapiens

<400> SEQUENCE: 25

```
Gln Met Arg Lys Leu Thr Ser Asn Leu Arg Ile Gly Phe Gly Ala
1               5                   10                  15
```

<210> SEQ ID NO 26
<211> LENGTH: 15
<212> TYPE: PRT
<213> ORGANISM: Homo sapiens

<400> SEQUENCE: 26

```
Ile Gly Phe Gly Ala Phe Val Asp Lys Pro Val Ser Pro Tyr Met
1               5                   10                  15
```

<210> SEQ ID NO 27
<211> LENGTH: 15
<212> TYPE: PRT
<213> ORGANISM: Homo sapiens

<400> SEQUENCE: 27

```
Val Ser Pro Tyr Met Tyr Ile Ser Pro Pro Glu Ala Leu Glu Asn
1               5                   10                  15
```

<210> SEQ ID NO 28
<211> LENGTH: 15
<212> TYPE: PRT
<213> ORGANISM: Homo sapiens

<400> SEQUENCE: 28

```
Glu Ala Leu Glu Asn Pro Cys Tyr Asp Met Lys Thr Thr Cys Leu
1               5                   10                  15
```

<210> SEQ ID NO 29
<211> LENGTH: 15
<212> TYPE: PRT
<213> ORGANISM: Homo sapiens

<400> SEQUENCE: 29

```
Lys Thr Thr Cys Leu Pro Met Phe Gly Tyr Lys His Val Leu Thr
1               5                   10                  15
```

<210> SEQ ID NO 30
<211> LENGTH: 15
<212> TYPE: PRT
<213> ORGANISM: Homo sapiens

<400> SEQUENCE: 30

```
Lys His Val Leu Thr Leu Thr Asp Gln Val Thr Arg Phe Asn Glu
1               5                   10                  15
```

<210> SEQ ID NO 31
<211> LENGTH: 15
<212> TYPE: PRT
<213> ORGANISM: Homo sapiens

<400> SEQUENCE: 31

```
Thr Arg Phe Asn Glu Glu Val Lys Lys Gln Ser Val Ser Arg Asn
1               5                   10                  15
```

<210> SEQ ID NO 32
<211> LENGTH: 15
<212> TYPE: PRT
<213> ORGANISM: Homo sapiens

<400> SEQUENCE: 32

Ser Val Ser Arg Asn Arg Asp Ala Pro Glu Gly Gly Phe Asp Ala
1               5                   10                  15

<210> SEQ ID NO 33
<211> LENGTH: 15
<212> TYPE: PRT
<213> ORGANISM: Homo sapiens

<400> SEQUENCE: 33

Gly Gly Phe Asp Ala Ile Met Gln Ala Thr Val Cys Asp Glu Lys
1               5                   10                  15

<210> SEQ ID NO 34
<211> LENGTH: 15
<212> TYPE: PRT
<213> ORGANISM: Homo sapiens

<400> SEQUENCE: 34

Val Cys Asp Glu Lys Ile Gly Trp Arg Asn Asp Ala Ser His Leu
1               5                   10                  15

<210> SEQ ID NO 35
<211> LENGTH: 15
<212> TYPE: PRT
<213> ORGANISM: Homo sapiens

<400> SEQUENCE: 35

Asp Ala Ser His Leu Leu Val Phe Thr Thr Asp Ala Lys Thr His
1               5                   10                  15

<210> SEQ ID NO 36
<211> LENGTH: 15
<212> TYPE: PRT
<213> ORGANISM: Homo sapiens

<400> SEQUENCE: 36

Asp Ala Lys Thr His Ile Ala Leu Asp Gly Arg Leu Ala Gly Ile
1               5                   10                  15

<210> SEQ ID NO 37
<211> LENGTH: 15
<212> TYPE: PRT
<213> ORGANISM: Homo sapiens

<400> SEQUENCE: 37

Arg Leu Ala Gly Ile Val Gln Pro Asn Asp Gly Gln Cys His Val
1               5                   10                  15

<210> SEQ ID NO 38
<211> LENGTH: 15
<212> TYPE: PRT
<213> ORGANISM: Homo sapiens

<400> SEQUENCE: 38

Gly Gln Cys His Val Gly Ser Asp Asn His Tyr Ser Ala Ser Thr
1               5                   10                  15

<210> SEQ ID NO 39

```
<211> LENGTH: 15
<212> TYPE: PRT
<213> ORGANISM: Homo sapiens

<400> SEQUENCE: 39

Tyr Ser Ala Ser Thr Thr Met Asp Tyr Pro Ser Leu Gly Leu Met
1               5                   10                  15

<210> SEQ ID NO 40
<211> LENGTH: 15
<212> TYPE: PRT
<213> ORGANISM: Homo sapiens

<400> SEQUENCE: 40

Ser Leu Gly Leu Met Thr Glu Lys Leu Ser Gln Lys Asn Ile Asn
1               5                   10                  15

<210> SEQ ID NO 41
<211> LENGTH: 15
<212> TYPE: PRT
<213> ORGANISM: Homo sapiens

<400> SEQUENCE: 41

Gln Lys Asn Ile Asn Leu Ile Phe Ala Val Thr Glu Asn Val Val
1               5                   10                  15

<210> SEQ ID NO 42
<211> LENGTH: 15
<212> TYPE: PRT
<213> ORGANISM: Homo sapiens

<400> SEQUENCE: 42

Thr Glu Asn Val Val Asn Leu Tyr Gln Asn Tyr Ser Glu Leu Ile
1               5                   10                  15

<210> SEQ ID NO 43
<211> LENGTH: 15
<212> TYPE: PRT
<213> ORGANISM: Homo sapiens

<400> SEQUENCE: 43

Tyr Ser Glu Leu Ile Pro Gly Thr Thr Val Gly Val Leu Ser Met
1               5                   10                  15

<210> SEQ ID NO 44
<211> LENGTH: 15
<212> TYPE: PRT
<213> ORGANISM: Homo sapiens

<400> SEQUENCE: 44

Gly Val Leu Ser Met Asp Ser Ser Asn Val Leu Gln Leu Ile Val
1               5                   10                  15

<210> SEQ ID NO 45
<211> LENGTH: 15
<212> TYPE: PRT
<213> ORGANISM: Homo sapiens

<400> SEQUENCE: 45

Leu Gln Leu Ile Val Asp Ala Tyr Gly Lys Ile Arg Ser Lys Val
1               5                   10                  15

<210> SEQ ID NO 46
<211> LENGTH: 15
<212> TYPE: PRT
<213> ORGANISM: Homo sapiens
```

-continued

<400> SEQUENCE: 46

Ile Arg Ser Lys Val Glu Leu Glu Val Arg Asp Leu Pro Glu Glu
1               5                   10                  15

<210> SEQ ID NO 47
<211> LENGTH: 15
<212> TYPE: PRT
<213> ORGANISM: Homo sapiens

<400> SEQUENCE: 47

Asp Leu Pro Glu Glu Leu Ser Leu Ser Phe Asn Ala Thr Cys Leu
1               5                   10                  15

<210> SEQ ID NO 48
<211> LENGTH: 15
<212> TYPE: PRT
<213> ORGANISM: Homo sapiens

<400> SEQUENCE: 48

Asn Ala Thr Cys Leu Asn Asn Glu Val Ile Pro Gly Leu Lys Ser
1               5                   10                  15

<210> SEQ ID NO 49
<211> LENGTH: 15
<212> TYPE: PRT
<213> ORGANISM: Homo sapiens

<400> SEQUENCE: 49

Pro Gly Leu Lys Ser Cys Met Gly Leu Lys Ile Gly Asp Thr Val
1               5                   10                  15

<210> SEQ ID NO 50
<211> LENGTH: 15
<212> TYPE: PRT
<213> ORGANISM: Homo sapiens

<400> SEQUENCE: 50

Ile Gly Asp Thr Val Ser Phe Ser Ile Glu Ala Lys Val Arg Gly
1               5                   10                  15

<210> SEQ ID NO 51
<211> LENGTH: 15
<212> TYPE: PRT
<213> ORGANISM: Homo sapiens

<400> SEQUENCE: 51

Ala Lys Val Arg Gly Cys Pro Gln Glu Lys Glu Lys Ser Phe Thr
1               5                   10                  15

<210> SEQ ID NO 52
<211> LENGTH: 15
<212> TYPE: PRT
<213> ORGANISM: Homo sapiens

<400> SEQUENCE: 52

Glu Lys Ser Phe Thr Ile Lys Pro Val Gly Phe Lys Asp Ser Leu
1               5                   10                  15

<210> SEQ ID NO 53
<211> LENGTH: 15
<212> TYPE: PRT
<213> ORGANISM: Homo sapiens

<400> SEQUENCE: 53

```
Phe Lys Asp Ser Leu Ile Val Gln Val Thr Phe Asp Cys Asp Cys
1               5                  10                  15

<210> SEQ ID NO 54
<211> LENGTH: 15
<212> TYPE: PRT
<213> ORGANISM: Homo sapiens

<400> SEQUENCE: 54

Phe Asp Cys Asp Cys Ala Cys Gln Ala Gln Ala Glu Pro Asn Ser
1               5                  10                  15

<210> SEQ ID NO 55
<211> LENGTH: 15
<212> TYPE: PRT
<213> ORGANISM: Homo sapiens

<400> SEQUENCE: 55

Ala Glu Pro Asn Ser His Arg Cys Asn Asn Gly Asn Gly Thr Phe
1               5                  10                  15

<210> SEQ ID NO 56
<211> LENGTH: 15
<212> TYPE: PRT
<213> ORGANISM: Homo sapiens

<400> SEQUENCE: 56

Gly Asn Gly Thr Phe Glu Cys Gly Val Cys Arg Cys Gly Pro Gly
1               5                  10                  15

<210> SEQ ID NO 57
<211> LENGTH: 15
<212> TYPE: PRT
<213> ORGANISM: Homo sapiens

<400> SEQUENCE: 57

Arg Cys Gly Pro Gly Trp Leu Gly Ser Gln Cys Glu Cys Ser Glu
1               5                  10                  15

<210> SEQ ID NO 58
<211> LENGTH: 15
<212> TYPE: PRT
<213> ORGANISM: Homo sapiens

<400> SEQUENCE: 58

Cys Glu Cys Ser Glu Glu Asp Tyr Arg Pro Ser Gln Gln Asp Glu
1               5                  10                  15

<210> SEQ ID NO 59
<211> LENGTH: 15
<212> TYPE: PRT
<213> ORGANISM: Homo sapiens

<400> SEQUENCE: 59

Ser Gln Gln Asp Glu Cys Ser Pro Arg Glu Gly Gln Pro Val Cys
1               5                  10                  15

<210> SEQ ID NO 60
<211> LENGTH: 15
<212> TYPE: PRT
<213> ORGANISM: Homo sapiens

<400> SEQUENCE: 60

Gly Gln Pro Val Cys Ser Gln Arg Gly Glu Cys Leu Cys Gly Gln
1               5                  10                  15
```

```
<210> SEQ ID NO 61
<211> LENGTH: 15
<212> TYPE: PRT
<213> ORGANISM: Homo sapiens

<400> SEQUENCE: 61

Cys Leu Cys Gly Gln Cys Val Cys His Ser Ser Asp Phe Gly Lys
1               5                   10                  15

<210> SEQ ID NO 62
<211> LENGTH: 15
<212> TYPE: PRT
<213> ORGANISM: Homo sapiens

<400> SEQUENCE: 62

Ser Asp Phe Gly Lys Ile Thr Gly Lys Tyr Cys Glu Cys Asp Asp
1               5                   10                  15

<210> SEQ ID NO 63
<211> LENGTH: 15
<212> TYPE: PRT
<213> ORGANISM: Homo sapiens

<400> SEQUENCE: 63

Cys Glu Cys Asp Asp Phe Ser Cys Val Arg Tyr Lys Gly Glu Met
1               5                   10                  15

<210> SEQ ID NO 64
<211> LENGTH: 15
<212> TYPE: PRT
<213> ORGANISM: Homo sapiens

<400> SEQUENCE: 64

Tyr Lys Gly Glu Met Cys Ser Gly His Gly Gln Cys Ser Cys Gly
1               5                   10                  15

<210> SEQ ID NO 65
<211> LENGTH: 15
<212> TYPE: PRT
<213> ORGANISM: Homo sapiens

<400> SEQUENCE: 65

Gln Cys Ser Cys Gly Asp Cys Leu Cys Asp Ser Asp Trp Thr Gly
1               5                   10                  15

<210> SEQ ID NO 66
<211> LENGTH: 15
<212> TYPE: PRT
<213> ORGANISM: Homo sapiens

<400> SEQUENCE: 66

Ser Asp Trp Thr Gly Tyr Tyr Cys Asn Cys Thr Thr Arg Thr Asp
1               5                   10                  15

<210> SEQ ID NO 67
<211> LENGTH: 15
<212> TYPE: PRT
<213> ORGANISM: Homo sapiens

<400> SEQUENCE: 67

Thr Thr Arg Thr Asp Thr Cys Met Ser Ser Asn Gly Leu Leu Cys
1               5                   10                  15

<210> SEQ ID NO 68
<211> LENGTH: 15
```

```
<212> TYPE: PRT
<213> ORGANISM: Homo sapiens

<400> SEQUENCE: 68

Asn Gly Leu Leu Cys Ser Gly Arg Gly Lys Cys Glu Cys Gly Ser
1               5                   10                  15

<210> SEQ ID NO 69
<211> LENGTH: 15
<212> TYPE: PRT
<213> ORGANISM: Homo sapiens

<400> SEQUENCE: 69

Cys Glu Cys Gly Ser Cys Val Cys Ile Gln Pro Gly Ser Tyr Gly
1               5                   10                  15

<210> SEQ ID NO 70
<211> LENGTH: 15
<212> TYPE: PRT
<213> ORGANISM: Homo sapiens

<400> SEQUENCE: 70

Pro Gly Ser Tyr Gly Asp Thr Cys Glu Lys Cys Pro Thr Cys Pro
1               5                   10                  15

<210> SEQ ID NO 71
<211> LENGTH: 15
<212> TYPE: PRT
<213> ORGANISM: Homo sapiens

<400> SEQUENCE: 71

Cys Pro Thr Cys Pro Asp Ala Cys Thr Phe Lys Lys Glu Cys Val
1               5                   10                  15

<210> SEQ ID NO 72
<211> LENGTH: 15
<212> TYPE: PRT
<213> ORGANISM: Homo sapiens

<400> SEQUENCE: 72

Lys Lys Glu Cys Val Glu Cys Lys Lys Phe Asp Arg Gly Ala Leu
1               5                   10                  15

<210> SEQ ID NO 73
<211> LENGTH: 15
<212> TYPE: PRT
<213> ORGANISM: Homo sapiens

<400> SEQUENCE: 73

Asp Arg Gly Ala Leu His Asp Glu Asn Thr Cys Asn Arg Tyr Cys
1               5                   10                  15

<210> SEQ ID NO 74
<211> LENGTH: 15
<212> TYPE: PRT
<213> ORGANISM: Homo sapiens

<400> SEQUENCE: 74

Cys Asn Arg Tyr Cys Arg Asp Glu Ile Glu Ser Val Lys Glu Leu
1               5                   10                  15

<210> SEQ ID NO 75
<211> LENGTH: 15
<212> TYPE: PRT
<213> ORGANISM: Homo sapiens
```

```
<400> SEQUENCE: 75

Ser Val Lys Glu Leu Lys Asp Thr Gly Lys Asp Ala Val Asn Cys
1               5                   10                  15

<210> SEQ ID NO 76
<211> LENGTH: 15
<212> TYPE: PRT
<213> ORGANISM: Homo sapiens

<400> SEQUENCE: 76

Asp Ala Val Asn Cys Thr Tyr Lys Asn Glu Asp Cys Val Val
1               5                   10                  15

<210> SEQ ID NO 77
<211> LENGTH: 15
<212> TYPE: PRT
<213> ORGANISM: Homo sapiens

<400> SEQUENCE: 77

Asp Asp Cys Val Val Arg Phe Gln Tyr Tyr Glu Asp Ser Ser Gly
1               5                   10                  15

<210> SEQ ID NO 78
<211> LENGTH: 15
<212> TYPE: PRT
<213> ORGANISM: Homo sapiens

<400> SEQUENCE: 78

Glu Asp Ser Ser Gly Lys Ser Ile Leu Tyr Val Val Glu Glu Pro
1               5                   10                  15

<210> SEQ ID NO 79
<211> LENGTH: 15
<212> TYPE: PRT
<213> ORGANISM: Homo sapiens

<400> SEQUENCE: 79

Val Val Glu Glu Pro Glu Cys Pro Lys Gly Pro Asp Ile Leu Val
1               5                   10                  15

<210> SEQ ID NO 80
<211> LENGTH: 15
<212> TYPE: PRT
<213> ORGANISM: Homo sapiens

<400> SEQUENCE: 80

Pro Asp Ile Leu Val Val Leu Leu Ser Val Met Gly Ala Ile Leu
1               5                   10                  15

<210> SEQ ID NO 81
<211> LENGTH: 15
<212> TYPE: PRT
<213> ORGANISM: Homo sapiens

<400> SEQUENCE: 81

Met Gly Ala Ile Leu Leu Ile Gly Leu Ala Ala Leu Leu Ile Trp
1               5                   10                  15

<210> SEQ ID NO 82
<211> LENGTH: 15
<212> TYPE: PRT
<213> ORGANISM: Homo sapiens

<400> SEQUENCE: 82

Ala Leu Leu Ile Trp Lys Leu Leu Ile Thr Ile His Asp Arg Lys
```

-continued

```
1               5                  10                  15

<210> SEQ ID NO 83
<211> LENGTH: 15
<212> TYPE: PRT
<213> ORGANISM: Homo sapiens

<400> SEQUENCE: 83

Ile His Asp Arg Lys Glu Phe Ala Lys Phe Glu Glu Arg Ala
1               5                  10                  15

<210> SEQ ID NO 84
<211> LENGTH: 15
<212> TYPE: PRT
<213> ORGANISM: Homo sapiens

<400> SEQUENCE: 84

Glu Glu Glu Arg Ala Arg Ala Lys Trp Asp Thr Ala Asn Asn Pro
1               5                  10                  15

<210> SEQ ID NO 85
<211> LENGTH: 15
<212> TYPE: PRT
<213> ORGANISM: Homo sapiens

<400> SEQUENCE: 85

Thr Ala Asn Asn Pro Leu Tyr Lys Glu Ala Thr Ser Thr Phe Thr
1               5                  10                  15

<210> SEQ ID NO 86
<211> LENGTH: 15
<212> TYPE: PRT
<213> ORGANISM: Homo sapiens

<400> SEQUENCE: 86

Lys Glu Ala Thr Ser Thr Phe Thr Asn Ile Thr Tyr Arg Gly Thr
1               5                  10                  15
```

USE OF PLATELET GLYCOPEPTIDE IIIA EPITOPES IN THE TREATMENT OF IMMUNE THROMBOCYTOPENIC PURPURA

This patent application is a U.S. National Stage Application of International Application No. PCT/EP2008/050595, filed Jan. 18, 2008, which claims the benefit of priority from Great Britain Application No. 0701048.1, filed Jan. 18, 2007, teachings of each of which are herein incorporated by reference in their entirety.

The present invention relates to a composition for treating diseases associated with autoantibodies specific for platelet proteins, in particular autoimmune thrombocytopenic purpura.

Chronic autoimmune thrombocytopenic purpura (AITP) is a bleeding disorder characterized by the production of autoantibodies that mediate platelet destruction. The clinical signs include petechial hemorrhages, hemorrhagic bullae on mucous membranes, gingival or gastrointestinal bleeding, menorrhagia, retinal hemorrhages, and, most seriously, intracranial hemorrhage. Current therapeutic strategies for AITP rely on non-specific immunosuppressive agents, or intravenous immunoglobulin or anti-D, with refractory cases undergoing splenectomy to remove a major site of autoantibody production and platelet destruction. Unfortunately, the results of these approaches are frequently unsatisfactory. A fuller understanding of the pathogenesis of AITP is therefore required, in order to develop safe, effective treatments that specifically inhibit the disease process.

A major focus of research into the pathogenesis of AITP has been the characterization of the autoantibody response. Platelet membrane glycoprotein IIb/IIIa (GPIIb/IIIa) has emerged as the major autoantigen that is bound by pathogenic autoantibodies from most patients. Other platelet antigens that can be targeted, but less frequently, include glycoproteins GPIb/IX, GPIa/IIa, and GPV. Although this progress in determining the specificities of the autoantibodies has led to novel diagnostic assays for AITP, the mechanisms underlying the loss of self-tolerance remain to be elucidated.

The vast majority of IgG responses are driven by $CD4^+$ helper T (Th) cells, including the production of pathogenic antibodies in murine models of autoimmune blood cell destruction. Human AITP is no exception, since the disease is associated with loss of peripheral T cell tolerance and the development of recall helper responses to platelet autoantigens. Peripheral blood Th cells from AITP patients, in comparison with those from healthy controls, exhibit accelerated proliferation when stimulated in vitro with fragments of purified or recombinant GPIIb/IIIa, indicative of prior activation in vivo. These memory Th cells are capable of driving anti-GPIIb/IIIa IgG synthesis by peripheral blood B cells from patients in vitro, with the spleen as the primary site for the autoreactive B cells to receive such help in vivo. T cells in AITP may, in addition to providing help for the autoantibody response, also contribute directly to platelet destruction. In response to the accumulating evidence that Th cells represent potential therapeutic targets, a small number of AITP patients has been treated with a humanized monoclonal antibody (mAb) that blocks the helper co-stimulatory molecule, CD40 ligand (CD154). The effects were to reduce both the frequency and in vitro collaboration of peripheral blood Th and B cells responsive to GPIIb/IIIa, and in some cases, treatment was associated with increased platelet counts. It is considered that any such immune inhibition may be only temporary, and not necessarily limited to the pathogenic response.

According to the present invention there is provided a composition for treating diseases associated with autoantibodies specific for platelet proteins by tolerisation, the composition comprising an epitope of the platelet protein.

Tolerisation is an effective way to treat autoimmune diseases. $CD4^+$ Th cells recognize short peptides that have been processed and displayed bound to MHC class II molecules by antigen presenting cells (APC). Antigen-specific tolerance can be induced in vivo by synthetic peptides containing dominant helper epitopes, if administered appropriately in soluble form, for example via mucosal surfaces in the nose or gut.

It has been shown that peptides containing dominant Th cell epitopes can prevent responses to the corresponding antigen when given in soluble form without adjuvant, or if administered by a tolerogenic route e.g. mucosal. Importantly, induction to tolerance to only one dominant epitope, particularly if mediated by active immune regulation, can ablate responsiveness to the entire autoantigen from which it is derived, and also to other, associated antigens by a process of bystander suppression.

In the present invention, peptides that contain the dominant Th epitopes from platelet autoantigens were mapped.

The mapping took place by screening a panel of short, overlapping peptides spanning the entire sequence of platelet glycoprotein for the ability to stimulate recall responses by peripheral blood Th cells.

Conveniently the platelet protein is a membrane component.

Membrane proteins are highly involved in stimulating autoimmune responses.

Conveniently the platelet protein is GPIIIa.

GPIIIa is a major autoantigenic molecule, which is known to contain important B and T cell determinants. The present invention identifies GPIIIa peptides that contain epitopes recognized by autoreactive Th cells from AITP patients, and which are candidate tolerogens for specific immunotherapy of the disease and describes seven dominant sequences.

Autoreactive Th cells specific for platelet glycoprotein are known to be activated in AITP, but this is the first time that peptides driving the response have been mapped. The results not only provide further insight into the mechanisms of disease, but open the way for novel forms of peptide immunotherapy for AITP that selectively target the pathogenic Th cells.

Conveniently the disease is autoimmune thrombocytopenic purpura.

The need for specific, effective and safe treatment for patients with chronic AITP may be met by the development of peptide immunotherapy to re-induce Th tolerance to the platelet glycoproteins.

The composition can be formulated for various types of administration including through oral, rectal, nasal, buccal, dermal, topical, parenteral, intraarticular, inhalation, intrathecal and vaginal forms of administration.

Conveniently the composition is formulated for delivery through non-invasive routes. The composition may be formulated for delivery through mucosal tissue.

Alternatively, the composition is formulated for delivery through invasive routes such as injection, for example intraperitoneal, intramuscular, or depot injections, or via implants.

Any of the aforementioned routes can lead to effective tolerisation.

Conveniently the epitope is immunodominant.

Immunodominance ensures that effective tolerisation takes place.

Conveniently the epitope is promiscuous.

Promiscuous epitopes elicit responses regardless of the HLA type of the patient. Accordingly, the epitopes can be used over a wider range of the population.

Conveniently the epitope contains between substantially 10 and 20 amino acids. The epitope may contain substantially 15 amino acids.

Such lengths of epitope result in effective tolerisation.

Conveniently the epitope is selected from SEQ ID No: 2, 44, 47, 53, 70, 77 and 82.

In the example of the present invention PBMC from almost all patients with AITP proliferated against members of a peptide panel spanning the sequence of GPIIIa, and such responses are strongly associated with the disease since they were rarely exhibited by samples from healthy or disease control donors. The culture conditions were biased in favor of supporting accelerated recall responses by Th cells that have previously been activated in vivo as part of the disease process, and not by naïve Th cells. The vast majority of the patients with AITP had both anti-GPIIb/IIIa antibodies and PBMC that mount recall proliferation to GPIIIa peptides, strengthening the view that the pathogenic B cell response is dependent on T cell help specific for the same autoantigenic complex. The small number of AITP patients with PBMC responsive to GPIIIa peptides, but no detectable anti-GPIIb/IIIa antibodies, may reflect the limited serological assays that could be performed in these cases. As with other autoantigens, the relatively rare and weak responses to GPIIIa peptides observed in control donors could well represent cross-reactivity with environmental antigens, particularly given the limited sequence homology between different peptides necessary for T cell cross-reactivity. It was confirmed by flow cytometric analysis that the cells from patients with AITP that responded in vitro to immunodominant GPIIIa peptides were of the $CD3^+CD4^+$ Th phenotype, and the ability of anti-HLA antibodies consistently to block the proliferation verified that they were MHC class II restricted cells. DR appears to be the principal restricting locus, but the effects of the blocking antibodies suggest that DP and DQ molecules may also compete for presentation of particular GPIIIa peptides.

It has been shown in the present invention that multiple peptides from GPIIIa stimulated proliferation by Th cells from most AITP patients. This suggests that the diversity may follow the phenomenon of epitope spreading. This occurs when the autoimmune helper response initially targets very few, or only one, self-determinant(s), but further Th clones with new specificities for the same, or associated, autoantigens are recruited over time as pathology develops.

The related feature of GPIIIa recognition that resembles other autoaggressive responses is the variation, seen in individual AITP patients over time, in the peptides that induce proliferation by peripheral blood Th cells in vitro. Such gain or loss of stimulation by peptides can reflect changes in the frequency of the corresponding Th cells in the circulation, attributable to the respective effects of epitope spreading and clonal exhaustion.

It has also been shown that despite the variation between cases in the patterns of stimulatory GPIIIa peptides, particular sequences are dominant, and stimulate responses in many patients. Seven such peptides distributed throughout GPIIIa, were identified; numbers 2 (aa6-20), 44 (aa331-345), (aa361-375), 53 (aa421-435) 70 (aa591-605), 77 (aa661-675), 82 (aa711-725).

The question arises as to why these peptides should contain dominant epitopes. When considering conventional immune responses to foreign antigens, the dominant Th epitopes can often be predicted due to their ability to bind well to the restricting MHC molecules. However, the same is not true of many autoimmune diseases, where lack of tolerance in the helper compartment, whether mediated by deletion, anergy or regulation, is a prime factor in the selection of dominant helper epitopes, rather than high affinity for the restricting class II molecules. Indeed, there are well-characterized examples where inefficient presentation of self-peptides contributes crucially to the failure to tolerize the corresponding repertoire, and allows the persistence of potentially autoaggressive Th cells that can be activated to drive disease. AITP fits with this pattern, since many of the dominant peptides fail to exhibit high predicted affinity for any HLA-DR molecules from an extensive panel. Furthermore, with the exception of peptide 82 (aa711-725), for any of the dominant sequences that do carry an HLA-DR binding motif, there is no correlation in different patients between the expression of the respective class II molecule, and the stimulation of responses. The likely low affinity of most of the dominant GPIIIa peptides for their restricting MHC molecules would lead to poor presentation and could account for the escape of the corresponding Th cells from mechanisms that purge the immune repertoire of potentially autoaggressive lymphocytes. These Th cells would then be available to be activated in disease by events such as stimulation with higher avidity cross-reactive microbial antigens, or increased production and display of the dominant GPIIIa peptides following changes in antigen presentation in vivo. Th cells that recognize peptide 82 (aa711-725), may survive, not because of poor binding and display of the sequence by restricting MHC molecules, but because of "destructive processing" by enzymes that cleave the sequence within APC, although it should be noted that this peptide may be of less pathogenic relevance since it is the only dominant sequence to induce proliferation by Th cells from control donors.

Conveniently, a patient for which the composition is directed to is from Northern European Caucasian population. In this connection, ethnic origin can influence Th responses.

The invention will now be described, by way of illustration only, with reference to the following examples and the accompanying figures.

FIG. 1 shows that PBMC from patients with AITP proliferate in response to peptides from the sequence of GPIIIa. PBMC were isolated from representative patients AITP1 (A), AITP8 (B), AITP10 (C), and AITP20 (D) tested for the ability to proliferate against the panel of 86 peptides spanning the GPIIIa molecule. The line - - - denotes the level of proliferation taken as representing a significant positive response (SI>3).

Figure 2:
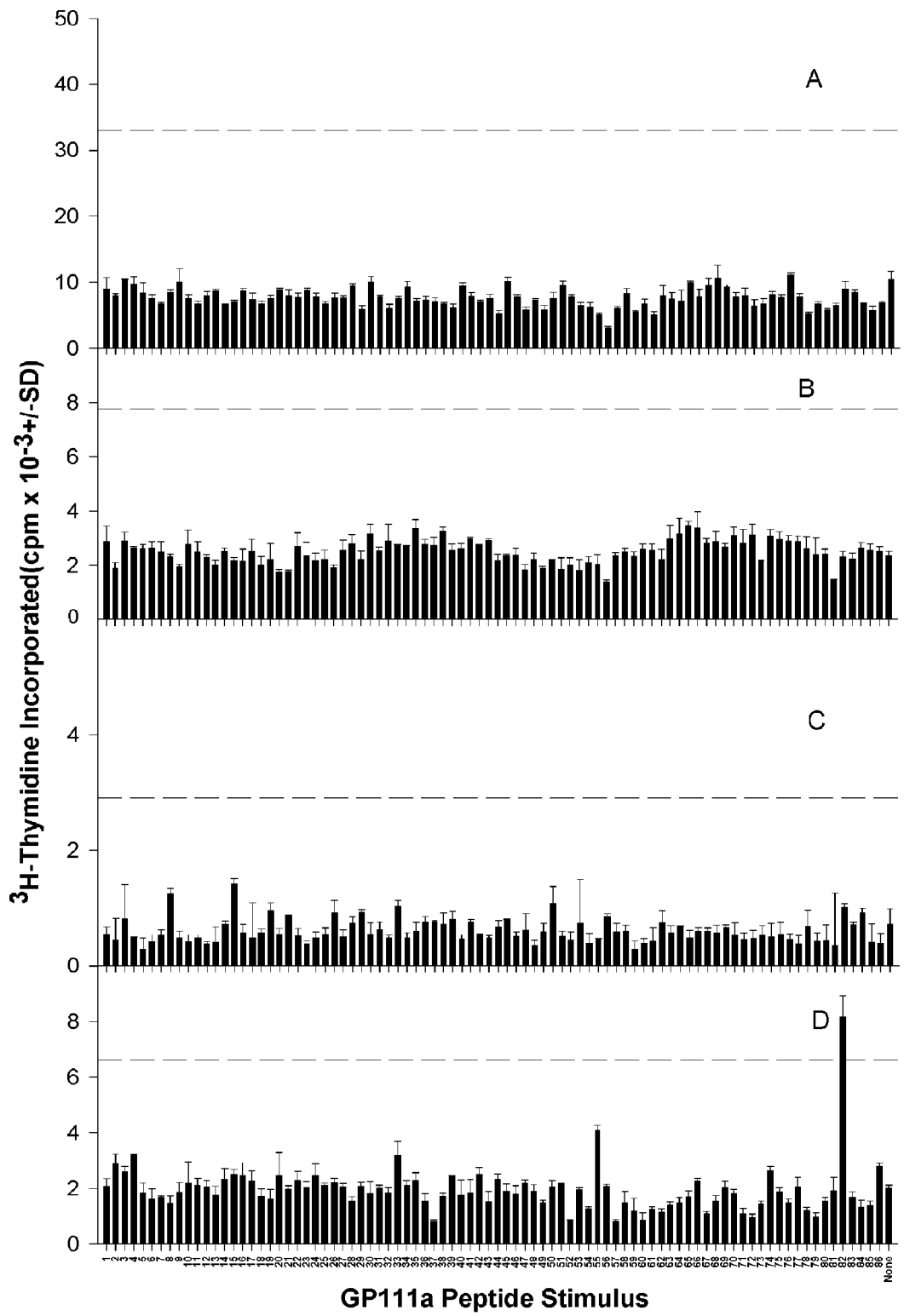

FIG. 2 shows that PBMC from healthy control donors rarely proliferate when stimulated with peptides from the GPIIIa sequence. Shown here are proliferative responses of PBMC from representative healthy control donors C5 (A), C6 (B), C8 (C) and C17 (D) against the panel of 86 peptides spanning the GPIIIa molecule. The line - - - denotes the level of proliferation taken as representing a significant positive response (SI>3).

Figure 3:
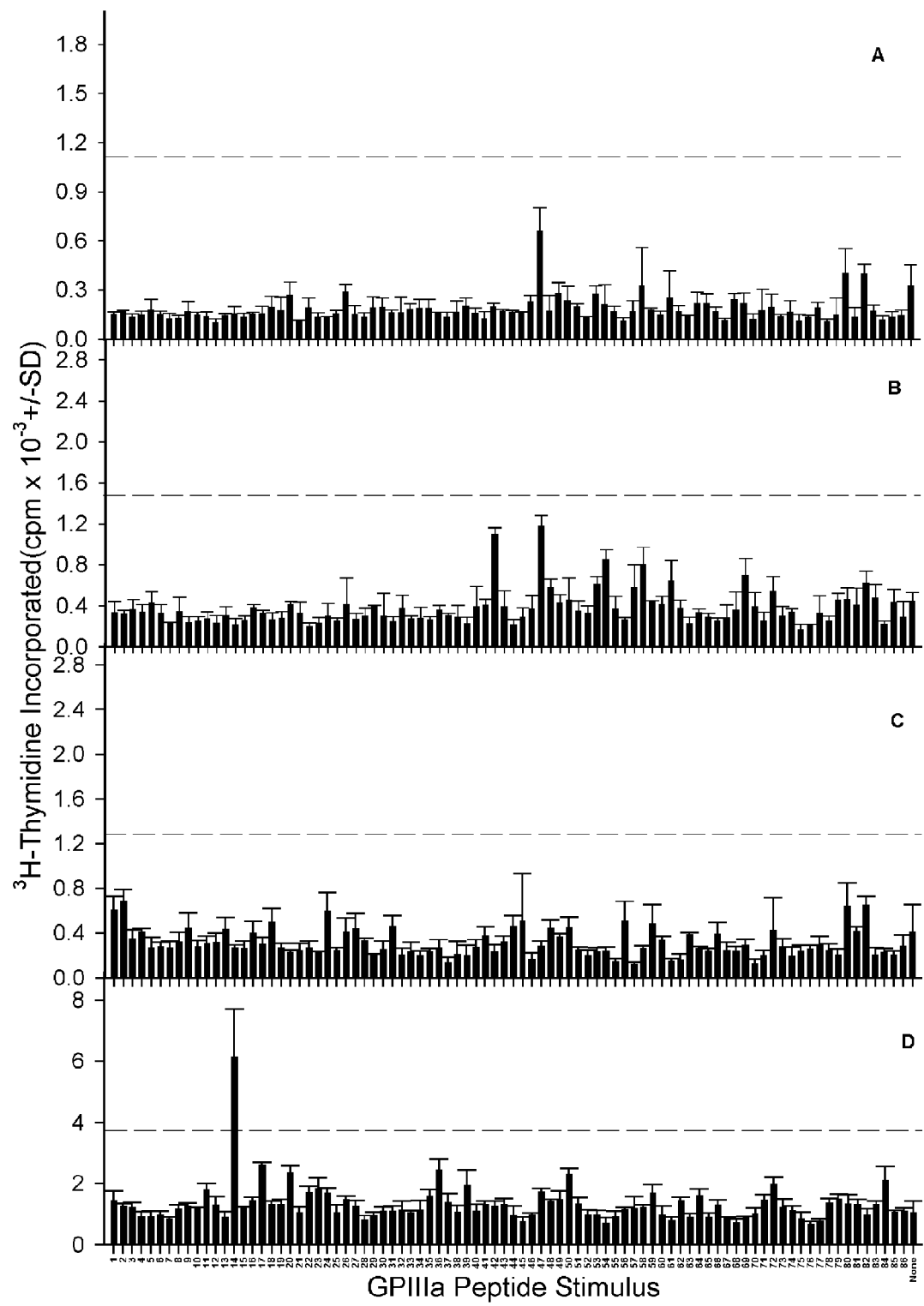

FIG. 3 shows that PBMC from disease control donors rarely proliferate when stimulated with peptides from the GPIIIa sequence. Shown here are proliferative responses of PBMC from representative patients with aplastic anemia C26 (A), C27 (B), C28 (C) and C29 (D) against the panel of 86 peptides spanning the GPIIIa molecule. The line - - - denotes the level of proliferation taken as representing a significant positive response (SI>3).

Figure 4:
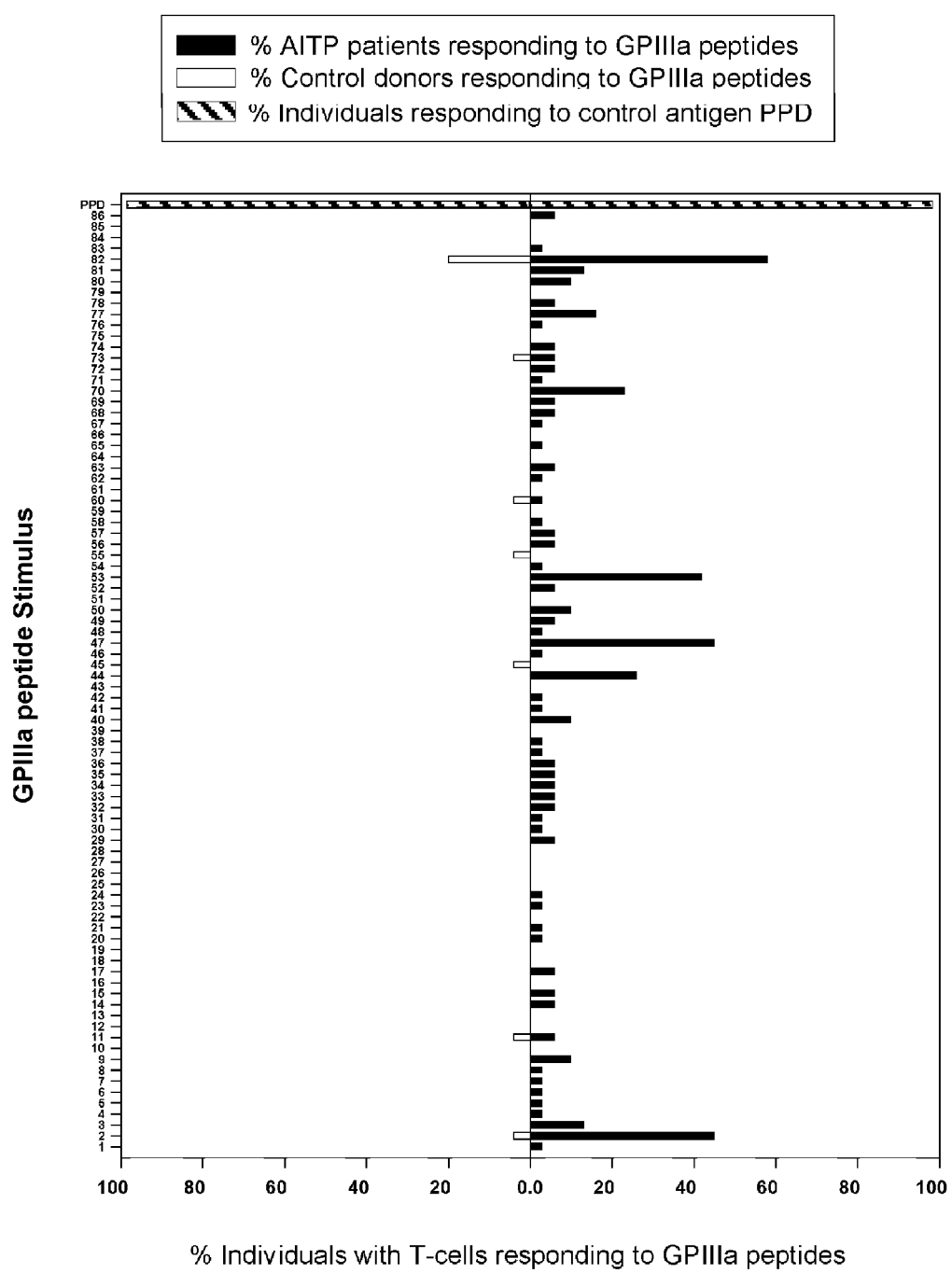

FIG. 4 shows that particular dominant peptides from GPIIIa stimulate T cells from many patients with AITP to proliferate. Shown here are the proportions of patients with AITP (solid) and healthy control donors (clear) whose PBMC proliferated in response to each of the 86 peptides from the panel spanning GPIIIa. PBMC from all individuals in both groups responded to stimulation with the control recall antigen mycobacterial PPD (hatched).

Figure 5:
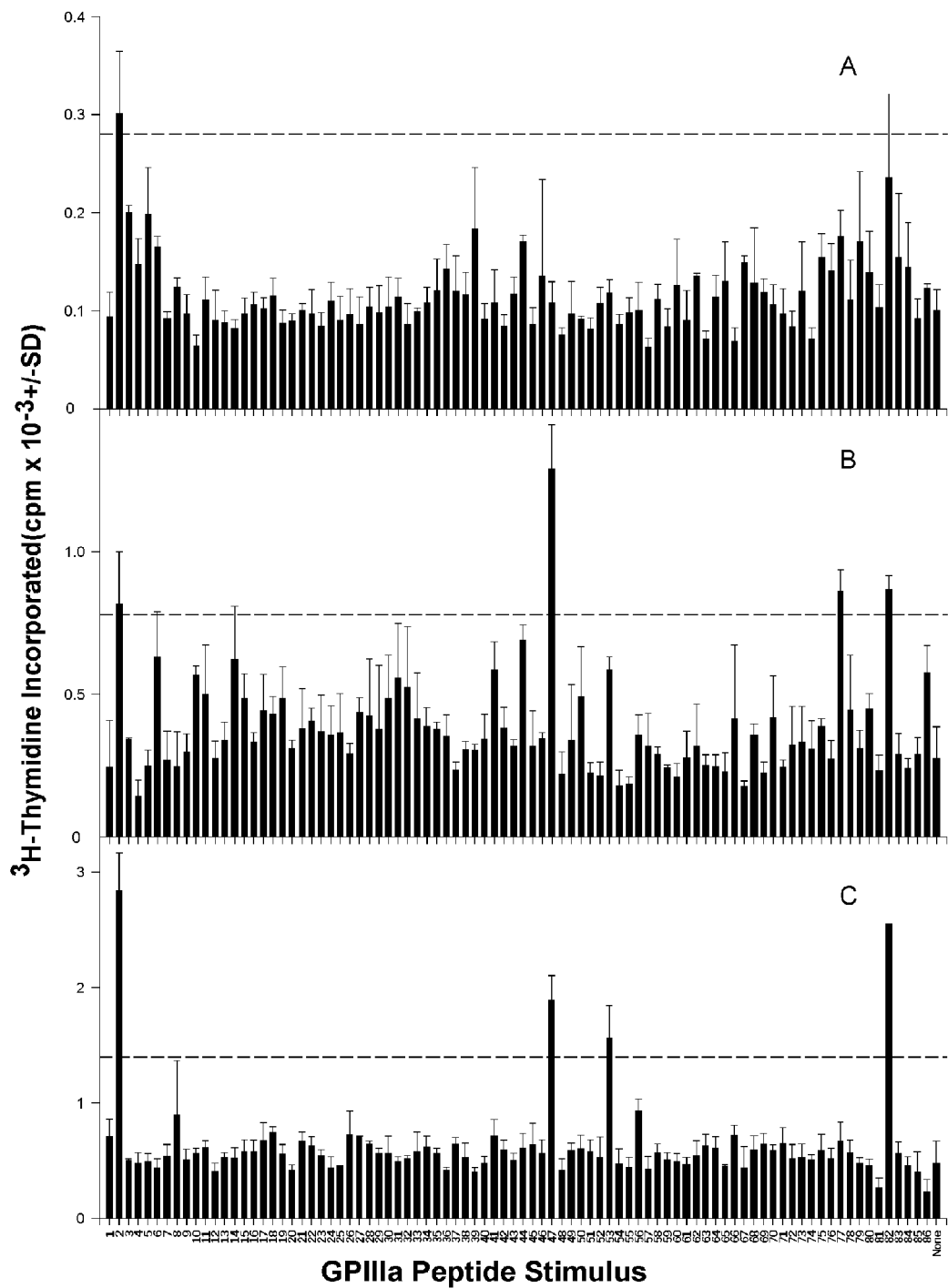

FIG. 5 shows that the pattern of GPIIIa peptides that stimulate PBMC from AITP patients to proliferate can evolve over time. Proliferative responses of PBMC from a representative patient (AITP22) against the panel of 86 peptides spanning the GPIIIa molecule were compared on three different occasions, at presentation (A; platelet count 76×109/L), then after 44 weeks (B; platelet count 54×109/L) and 56 weeks (C; platelet count 84×109/L). The line - - - denotes the level of proliferation taken as representing a significant positive response (SI>3).

Figure 6:
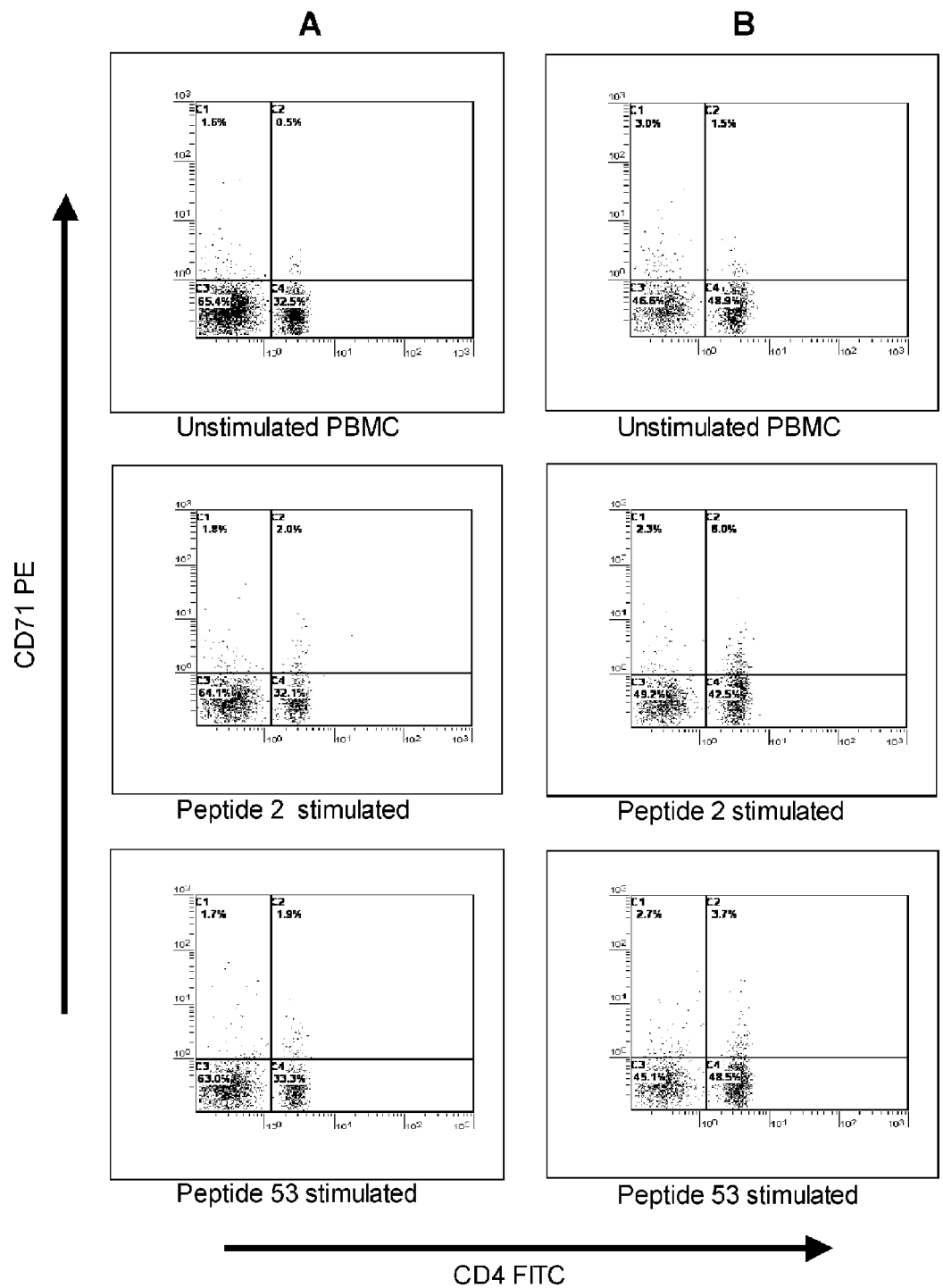

FIG. 6 shows that PBMC from patients with AITP that respond to GPIIIa peptides are predominantly of the helper phenotype. PBMC from patients AITP10 (A) and AITP18 (B) were either left unstimulated in culture, or incubated with GPIIIa peptides 2 or 53 that induce proliferative responses in these patients, before being stained for CD4 expression and the activation marker CD71. Results are shown gated on the CD3+ population.

Figure 7:

FIG. 7 shows that the proliferation of T cells from AITP patients against GPIIIa peptides is dependent on HLA-class II molecules. Cultures of PBMC from a representative patient (AITP9) were stimulated with dominant GPIIIa peptides 2, 47, 53 or 82, and class II restricted responses were blocked by addition of antibody specific for HLA-DR, -DQ or -DP. For each peptide stimulus, the line - - - denotes the level of inhibition taken as significant (>50%). Similar results were obtained with PBMC from another three patients.

EXAMPLE 1

Patients and Control Subjects

Approval for the study was received from the Grampian Local and Regional Ethics Committee (number 00/0052). Informed written consent was obtained from all patients and healthy controls. Samples of whole blood were obtained from 31 patients (21 female and 10 male) with AITP, who attended the outpatient hematology clinic at Aberdeen Royal Infirmary. The details of the patients, who are all North European Caucasian, are summarized in Table 1. The diagnosis of AITP was made by exclusion of other causes of thrombocytopenia and in compliance with the British Committee for Standards in Haematology Guideline. The majority (29/31) of the patients were being treated with immunosuppressive drugs at the time of sampling, and eight had undergone splenectomy.

Samples of whole blood for PBMC isolation were also taken from 25 healthy control blood donors (18 female and seven male). None was on any medication. PBMC samples from a further group, of five patients with aplastic anaemia (four male and one female), were included as disease controls, since this condition responds to immunosuppression and is considered to have an autoimmune basis, and patients also have low platelet counts.

Platelet Recovery and Preparation of Eluates

Platelets from AITP patients and controls were isolated by differential centrifugation of anti-coagulated (citrate-phosphate-dextrose) blood. Antibody was eluted from the surface of platelets as described by Hürlimann-Forster et al and stored at −80° C. until used.

Detection of Antiplatelet Autoantibodies Against GPIIb/IIIa from Serum and Platelet Eluates of AITP Patients and Controls Anti-GPIIb/IIIa autoantibody concentrations in sera and eluates were measured by ELISA using published methods of Bessos H et al in Vox Sang 1999; 77:103-106 and Sukati H et al in Transfusion 2005; 45:1165-1177. Briefly, samples were screened in duplicate wells of microtitre plates coated with purified GPIIb/IIIa. Background binding was determined by incubating each sample in uncoated wells, and control samples positive and negative for antibody were also included. Absorbance was read at 540 nm using a multiscan plate reader (Labsystems, Finland). Specific optical densities (OD)>0.1 and >0.05 were interpreted as positive results for serum and eluate samples respectively (determined from the mean of healthy control samples+2 SD).

HLA Class II DNA Typing Using PCR-SSP

Genomic DNA preparation from the whole blood of AITP patients and controls and HLA class II typing was carried using PCR-SSP as reported in Sukati H et al in Transfusion 2005; 45:1165-1177. Visual interpretation of positive bands after gel electrophoresis were confirmed using HELMBERG SCORE™ software v3.000T (provided by Dr. W. Helmberg, Institute for Transfusion Medicine, University of Graz, Austria, www.genoversion.com).

Preparation of Antigens and Mitogens

The human platelet membrane GPIIIa amino acid sequence (Genebank Accession no: M35999) was synthesized (Pepceuticals, Nottingham, UK) as a complete panel of 86 15-mer peptides, overlapping by 5-10 amino acids (Table 3). Peptide purity was monitored by amino acid analysis and mass spectrometry as reported previously by Barker R N et al in Blood 1997; 90:2701-2715, Scott L et al in Blood 2000; 96:4011-4019 and Cairns L S et al in J Am Soc Nephrol 2003; 14:2801-2812. The peptides were used for stimulation of T cells at the previously determined optimum concentration of 20 mg/mL in culture.

The antigen mycobacterial purified protein derivative (PPD) (Statens Serumintitut, Denmark) was added to cultures at 20 mg/mL to stimulate positive control recall T cell responses. Concanavalin A (Con A) (Sigma, Poole, Dorset, UK) was used at 20 mg/mL as a positive control T cell mitogen.

Isolation of Peripheral Blood Mononuclear Cells (PBMC)

Mononuclear cells were recovered from anti-coagulated samples of peripheral blood from AITP patients and control donors by density gradient centrifugation (Lymphoprep; Nycomed, Denmark). Cell viability determined by trypan blue exclusion was greater than 90% in all samples.

T Cell Proliferation Assay

Assays of T cell proliferation were carried out, as described by Scott L et al in Blood 2000; 96:4011-4019, Cairns L S et al in J Am Soc Nephrol 2003; 14:2801-2812 and Sukati H et al in Transfusion 2005; 45:1165-1177, under culture conditions designed to favor responses by previously activated T cells, rather than primary responses. Briefly, PBMC were cultured at 1.25×106 cells per mL in Alpha Modification of Eagle's Medium (Sigma, Poole, Dorset, UK) supplemented with 5% autologous serum. Synthetic GPIIIa peptides or control stimuli were added to cultures, which were incubated at 37° C. in a humidified atmosphere of 95% air and 5% $CO_2$. T cell proliferation was estimated from the incorporation of 3H-thymidine in triplicate 100 mL samples withdrawn from the cultures 5 days after stimulation, when recall responses peak. Results are presented either as the mean counts per minute (CPM)±SD of the triplicate samples, or as a stimulation index (SI) expressing the ratio of mean CPM in stimulated versus unstimulated control cultures. An SI>3 is interpreted as a positive response.

Flow Cytometric Characterization of Lymphocytes Responding to Stimulation

As previously described by Sukati H et al in Transfusion 2005; 45:1165-1177, cultures of unstimulated PBMC, and those proliferating in response to peptides, were analyzed for expression of the T cell marker CD3, the T helper marker CD4, and the activation marker CD71 by 3-colour flow cytometry. All antibodies and control immunoglobulins were supplied by Beckman Coulter (Bucks, UK). A total of 10,000 cells per sample was counted using an Epics XL cytometer (Beckman Coulter) and the results analyzed with Expo 32 software (Beckman Coulter).

HLA Restriction of PBMC Proliferating in Response to GPIIIa Peptides

To determine the HLA Class II restriction of proliferating T cells, 2.5 mg/mL anti-DR, anti-DQ or anti-DP blocking monoclonal antibodies (Pharmingen, Oxon, UK) were added to replicate cultures before stimulation.

Prediction of Peptide Binding Motifs for HLA-DR Molecules

Protein sequences were entered into ProPred predictive software (www.imtech.res.in/raghava/propred), which is based on quantitative matrices derived by Stumiolo T et al in Nat Biotechnol 1999; 17:555-561. An algorithm allows the sequences to be scanned for motifs predicted to have high affinity for binding to many of the commonly expressed HLA-DR molecules.

Statistical Analysis

Non-parametric Chi-square and Fisher Exact Tests were used for statistical analysis, with $p<0.05$ considered to represent significance.

Results

Mapping Peptides Derived from the GPIIIa Sequence that Stimulate Proliferation by PBMC from AITP Patients or Healthy Controls The prime aim was to identify the peptide sequences from GPIIIa that contain Th epitopes. PBMC were obtained from the group of 31 patients with AITP (clinical details summarized in Table 1) and from 25 healthy control blood donors. A panel of 86 synthetic overlapping 15-mer peptides, spanning the entire sequence of the platelet GPIIIa (Table 2) was screened for the ability to stimulate the proliferation of PBMC from each of the patients and controls. The platelet glycoprotein-responsive Th cells that are associated with AITP have previously been shown to be activated in vivo, as would be expected for autoaggressive lymphocytes of pathogenic relevance. Therefore, to map the epitopes recognized by these cells, the culture conditions were based on those previously designed to favor fast developing recall, rather than slower primary, responses.

Representative results from four AITP patients, demonstrating GPIIIa peptides that elicit PBMC proliferation, are illustrated in FIG. 1, and the stimulatory peptides for each of the 31 patients are listed in Table 3. It can be seen that PBMC from all but three patients responded to at least one member of the peptide panel, and that, typically, multiple sequences induced proliferation.

The presence of anti-platelet antibodies reactive with GPIIb/IIIa was confirmed in 27 of the 31 AITP patients (Table 3). The individuals generating anti-GPIIb/IIIa included 21 patients with serum antibodies, 14 of whom also had platelet-bound antibodies demonstrated after elution, plus a further six with no detectable serum antibodies but positive eluates. All eight patients who had undergone splenectomy had persisting antibodies. Comparison with the results of PBMC stimulation reveals that the vast majority of the AITP patients (25/31) had both anti-GPIIb/IIIa antibody and proliferative responses against GPIIIa peptides. This association between detectable anti-GPIIb/IIIa and peptide responsiveness is not absolute since, for example, three of the four antibody-negative patients did show PBMC proliferation to peptides. However, in these cases it was possible to screen only sera for anti-GPIIb/IIIa, and the testing of platelet eluates was often necessary to detect the antibody. Table 3 also illustrates that there is no simple relationship between the number, or the identities, of the stimulatory peptides and the platelet count of the AITP patients at the time of sampling.

In contrast to the results obtained in AITP patients, responses were rarely seen when the peptide panel was used to stimulate PBMC from healthy control donors. Examples of results from the control group are depicted in FIG. 2, with the data summarized in Table 4A. No anti-GPIIb/IIIa antibodies were detected in serum or platelet eluate samples from this group. PBMC from only nine of the control donors demonstrated proliferation to any of the peptide panel, and, in each of these cases, responsiveness was limited to one or two sequences. It should be noted that PBMC from all patients and control donors proliferated normally when stimulated with the control recall antigen mycobacterial PPD (FIG. 4) or the mitogen Con A (results not shown), indicating that any lack of response to the GPIIIa peptide panel is specific, and not attributable to a general loss of immune function or lymphocyte viability. The background levels of proliferation in the absence of antigen or mitogen are generally higher in the control donors than in the AITP patients, reflecting the effects of disease state and immunosuppressive treatment. The difference in the total number of peptide responses in the patient and control groups was highly significant (a total of 178 responses to peptides in 31 patients versus 12 in 25 healthy donors, $\chi2=115.967$; $p=<0.001$), consistent with the view that recall Th responses specific for platelet glycoprotein are associated with AITP. To confirm that responsiveness to GPIIIa epitopes is not a feature of immune mediated disease in general, or of low platelet counts, PBMC from a group of five patients with aplastic anemia were also stimulated with the peptide panel (results summarized in Table 4B, with representative examples illustrated in FIG. 3). It can be seen that, as in the healthy donors, responses to GPIIIa peptides in this disease control group are very infrequent.

Distribution of Stimulatory Peptides on the Platelet GPIIIa

Despite variation between AITP patients in the profile of GPIIIa peptides that elicited PBMC proliferation (Table 3), particular peptides were identified as dominant, since they stimulated responses in a high proportion of cases. These dominant sequences are shown in FIG. 4, which summarizes the number of patients in which each peptide induced proliferation. The four most dominant peptides are (aa6-20), 47 (aa361-375), 53 (aa421-435) and 82 (aa711-725), with 24 patients (77%) showing PBMC responses to at least one of these sequences, and 13 (42%) to three or more. A further three peptides, 44 (aa331-345), 70 (aa591-605) and 77 (aa661-675), exhibited a lower level of dominance, with each stimulating proliferation by PBMC from at least 5 (15%) patients.

Analysis of the GPIIIa peptides eliciting the relatively rare responses by control donor PBMC (Table 4, FIG. 4) reveals that they include only one of the seven sequences identified as dominant in AITP patients. This peptide, 82 (aa711-725), was the only member of the entire panel to stimulate PBMC from more than one control donor. Thus, compared to those from AITP patients, the responses of healthy control PBMC to GPIIIa sequences are not only infrequent, but generally target sporadic peptides that differ from those commonly recognized in AITP.

Variation Over Time in the Pattern of GPIIIa Peptides that Stimulate Responses

Longitudinal studies of patients with chronic autoimmune diseases other than AITP demonstrate changes over time in the identities of autoantigen-derived peptides recognized by autoaggressive Th cells. To establish whether the same is true for AITP, serial PBMC samples taken over periods of weeks or months from patients (n=10) were screened for responsiveness to the GPIIIa peptide panel. FIG. 5 depicts a typical set of results, where the GPIIIa peptides were tested against PBMC taken from patient AITP22 on three different occasions over 56 weeks. The dominant peptide 2 (aa6-20) elicited proliferation from all samples, whilst responsiveness to dominant sequences 47 (aa361-375), 53 (aa421-435) and 82 (aa711-725) was initially absent but appeared at later time points, and proliferation to the lower ranking dominant peptide 77 (aa661-675) was seen only in the second sample. It should be noted that these differences are consistent across all replicate cultures set up from each sample, and therefore do not represent chance inter-well variation. These results from patient AITP-22, and the other examples, illustrate a complex, dynamic pattern of responsiveness, with some peptides persistently stimulating PBMC proliferation, and others eliciting responses that fluctuate over time. Such evolution of the fine specificity of the immune response does not directly correlate with the clinical course of disease, since there is no relationship between the changes over time in the identities of the stimulatory peptides, and the platelet count of the AITP patients (FIG. 5).

Characterization of the Phenotype of PBMC that Proliferate in Response to GPIIIa Peptides In order to confirm that the PBMC proliferating against GPIIIa peptides were of the $CD3^+CD4^+$ Th phenotype, selected cultures were analyzed by multi-color flow cytometry. Responding cells were labeled with antibody to the activation marker CD71, and the Th subset was identified by counter-staining with anti-CD3 and anti-CD4. Representative results (n=6) from two AITP patients are shown in FIG. 6. It can be seen that, as expected, the background level of CD71 expression in control, resting cultures was very low, and there was a small increase (1.5-3.8%) in numbers of activated $CD71^+$ cells after stimulation with dominant peptides 2 (aa6-20) or 53 (aa421-435). The size of this expansion is typical of the responses to antigen made by specific lymphocytes within a polyclonal population, and the vast majority (88-100%) of the cells that upregulated CD71 as a result of the peptide stimulation were $CD3^+CD4^+$.

Role of HLA Class II in Responses of PBMC from AITP Patients and Control Donors

In order to demonstrate functionally that the lymphocytes responding to GPIIIa peptides came from the Th subset, which is restricted by MHC Class II molecules, blocking antibodies specific for anti-HLA-DP, -DQ and -DR were tested for the ability to inhibit the responses. Dominant peptides 2(aa6-20), 47 (aa361-375), 53 (aa421-435) and 82 (aa711-725) were selected for these experiments and used to stimulate PBMC from four AITP patients, in the presence or absence of anti-DP, -DQ or DR. Representative results from one patient are illustrated in FIG. 7. Each example of peptide-induced proliferation was blocked by at least one of the antibodies, of which anti-DR was consistently the most potent, inhibiting 15 out of the 16 responses tested.

HLA type is one of the factors that can influence predisposition to particular immune-mediated diseases. The panels of AITP patients and healthy controls were typed for HLA-DR and HLA-DQ polymorphic beta chain genes (Tables 3 and 4A), and the results compared with published data from the general UK population. The commonest alleles at each locus amongst patients were, respectively, DRB1*03 and DRB1*15, and DQB1*03 and DQB1*06, but there were no significant positive or negative associations with the disease or the ability of particular sequences to stimulate proliferation.

Table 5 demonstrates that the dominant peptides are located throughout different domains of GPIIIa, including the transmembrane/cytoplasmic area, reflecting the fact that T cells, unlike pathogenic antibody, are not limited to the recognition of epitopes accessible on the intact cell. The selection of dominant helper epitopes in autoimmune disease may be also determined by different criteria from those that shape the fine specificity of conventional responses by $CD4^-$ T cells to foreign antigens. In particular, the major self-epitopes may be dominant due to a lack of tolerance in the corresponding Th cell repertoire, rather than because they are contained in the most efficiently presented peptides that exhibit high affinity for their restricting elements. To test whether this is true for AITP, a web-based algorithm (www.imtech.res.in/raghava/propred) was used to predict the motifs within the sequence of GPIIIa that have high affinity for a comprehensive panel of HLA-DR molecules, including all those expressed by the AITP patients. The results in Table 5 reveal that three of the seven dominant GPIIIa peptides were predicted not to have high affinity for any of the class II molecules evaluated. Of the four dominant peptides computed to be displayed at high levels by particular HLA-DR molecules, only peptide 82 (aa711-725) showed a correlation ($\chi 2=10$; $p<0.05$) between the ability to stimulate Th responses and the expression of the relevant class II type by AITP patients. Thus, with the exception of peptide 82 (aa711-725), the vast majority of interactions between the dominant GPIIIa peptides and their restricting MHC molecules in AITP patients are predicted to be of low affinity.

TABLE 1

Clinical details of patients with AITP

| AITP Patients | Sex | Age [at Diagnosis] [Years] | Disease Duration [Years] | Platelet Count x $10^9$/L [at Diagnosis] | Treatment During Course of Disease | |
|---|---|---|---|---|---|---|
| | | | | | Corticosteroids | Splenectomy |
| AITP1 | F | 52 | 12 | 24 | PDL, AZP, DAP, IVIg | Yes |
| AITP2 | F | 55 | 4 | 2 | PDL, AZP | No |
| AITP3 | M | 60 | 3 | 5 | PDL, IVIg | No |
| AITP4 | M | 59 | 3 | 6 | PDL, IVIg | No |
| AITP5 | M | 64 | 2 | 2 | PDL | No |
| AITP6 | F | 83 | 4 | 5 | PDL, AZP, DAP | No |
| AITP7 | F | 35 | 7 | 3 | PDL, IVIg | No |
| AITP8 | M | 68 | 2 | 5 | PDL, DAP | No |
| AITP9 | F | 75 | 7 | 5 | PDL | No |
| AITP10 | F | 53 | 7 | 5 | PDL, IVIg | Yes |
| AITP11 | F | 31 | 2 | 4 | PDL | No |
| AITP12 | F | 61 | 11 | 3 | PDL, AZP | Yes |
| AITP13 | M | 54 | 2 | 2 | PDL | No |
| AITP14 | F | 31 | 1 | 68 | PDL, AZP, MYC | No |
| AITP15 | M | 79 | 2 | 5 | PDL, DAP, IVIg | Yes |
| AITP16 | M | 51 | 2 | 71 | NONE | No |
| AITP17 | F | 71 | 5 | 126 | PDL | No |
| AITP18 | F | 38 | 23 | 61 | PDL | No |
| AITP19 | M | 66 | 3 | 54 | PDL | No |
| AITP20 | F | 60 | 8 | 106 | NONE | No |
| AITP21 | F | 58 | 19 | 30 | PDL, AZP, DAP, IVIg | No |
| AITP22 | F | 74 | 2 | 20 | PDL | No |
| AITP23 | F | 69 | 7 | 6 | PDL, IVIg | Yes |
| AITP24 | F | 51 | 2 | 5 | PDL | Yes |
| AITP25 | F | 25 | 2 | 32 | PDL | No |
| AITP26 | M | 51 | 1 | 5 | PDL | No |

TABLE 1-continued

Clinical details of patients with AITP

| AITP Patients | Sex | Age [at Diagnosis] [Years] | Disease Duration [Years] | Platelet Count × 10⁹/L [at Diagnosis] | Treatment During Course of Disease | |
|---|---|---|---|---|---|---|
| | | | | | Corticosteroids | Splenectomy |
| AITP27 | F | 65 | 2 | 62 | PDL | No |
| AITP28 | M | 24 | 1 | 10 | PDL | No |
| AITP29 | F | 52 | 2 | 9 | PDL, DAP, IVIg, Cyclosporine | Yes |
| AITP30 | F | 76 | 4 | 121 | PDL | No |
| AITP31 | F | 45 | 1 | 36 | PDL, IVIg | Yes |

PDL = Prednisolone, AZP = Azathioprine; DAP = Dapsone; IVIg = Intravenous Immunoglobulin; MYC = Mycophenlate Mofetil

TABLE 2

Amino acid sequences of the panel of overlapping, synthetic GPIIIa peptides spanning the entire length of the GBIIIa molecule

| Sequence ID Number | Amino Acid Sequence | GPIIIa Residues |
|---|---|---|
| 1 | GPNICTTRGVSSCQQ | 1-15 |
| 2 | TTRGVSSCQQCLAVS | 6-20 |
| 3 | SSCQQCLAVSPMCAW | 11-25 |
| 4 | CLAVSPMCAWCSDEA | 16-30 |
| 5 | PMCAWCSDEALPLGS | 21-35 |
| 6 | CSDEALPLGSPRCDL | 26-40 |
| 7 | LPLGSPRCDLKENLL | 31-45 |
| 8 | PRCDLKENLLKDNCA | 36-50 |
| 9 | KENLLKDNCAPESIE | 41-55 |
| 10 | KDNCAPESIEFPVSE | 46-60 |
| 11 | PESIEFPVSEARVLE | 51-65 |
| 12 | FPVSEARVLEDRPLS | 56-70 |
| 13 | ARVLEDRPLSDKGSG | 61-75 |
| 14 | DRPLSDKGSGDSSQV | 66-80 |
| 15 | DKGSGDSSQVTQVSP | 71-85 |
| 16 | DSSQVTQVSPQRIAL | 76-90 |
| 17 | TQVSPQRIALRLRPD | 81-95 |
| 18 | QRIALRLRPDDSKNF | 86-100 |
| 19 | RLRPDDSKNFSIQVR | 91-105 |
| 20 | DSKNFSIQVRQVEDY | 96-110 |
| 21 | SIQVRQVEDYPVDIY | 101-115 |
| 22 | PVDIYYLMDLSYSMK | 111-125 |
| 23 | SYSMKDDLWSIQNLG | 121-135 |
| 24 | IQNLGTKLATQMRKL | 131-145 |
| 25 | QMRKLTSNLRIGFGA | 141-155 |
| 26 | IGFGAFVDKPVSPYM | 151-165 |
| 27 | VSPYMYISPPEALEN | 161-175 |
| 28 | EALENPCYDMKTTCL | 171-185 |
| 29 | KTTCLPMFGYKHVLT | 181-195 |
| 30 | KHVLTLTDQVTRFNE | 191-205 |
| 31 | TRFNEEVKKQSVSRN | 201-215 |
| 32 | SVSRNRDAPEGGFDA | 211-225 |
| 33 | GGFDAIMQATVCDEK | 221-235 |
| 34 | VCDEKIGWRNDASHL | 231-245 |
| 35 | DASHLLVFTTDAKTH | 241-255 |
| 36 | DAKTHIALDGRLAGI | 251-265 |
| 37 | RLAGIVQPNDGQCHV | 261-275 |
| 38 | GQCHVGSDNHYSAST | 271-285 |
| 39 | YSASTTMDYPSLGLM | 281-295 |
| 40 | SLGLMTEKLSQKNIN | 291-305 |
| 41 | QKNINLIFAVTENVV | 301-315 |
| 42 | TENVVNLYQNYSELI | 311-325 |
| 43 | YSELIPGTTVGVLSM | 321-335 |
| 44 | GVLSMDSSNVLQLIV | 331-345 |
| 45 | LQLIV DAYGK IRSKV | 341-355 |
| 46 | IRSKV ELEVR DLPEE | 351-365 |
| 47 | DLPEELSLSFNATCL | 361-375 |
| 48 | NATCLNNEVIPGLKS | 371-385 |
| 49 | PGLKSCMGLKIGDTV | 381-395 |
| 50 | IGDTVSFSIEAKVRG | 391-405 |
| 51 | AKVRGCPQEKEKSFT | 401-415 |
| 52 | EKSFTIKPVGFKDSL | 411-425 |
| 53 | FKDSLIVQVTFDCDC | 421-435 |
| 54 | FDCDCACQAQAEPNS | 431-445 |
| 55 | AEPNSHRCNNGNGTF | 441-455 |
| 56 | GNGTFECGVCRCGPG | 451-465 |
| 57 | RCGPGWLGSQCECSE | 461-475 |
| 58 | CECSE EDYRP SQQDE | 471-485 |
| 59 | SQQDECSPREGQPVC | 481-495 |
| 60 | GQPVCSQRGECLCGQ | 491-505 |
| 61 | CLCGQCVCHSSDFGK | 501-515 |

TABLE 2-continued

Amino acid sequences of the panel of overlapping, synthetic GPIIIa peptides spanning the entire length of the GBIIIa molecule

| Sequence ID Number | Amino Acid Sequence | GPIIIa Residues |
|---|---|---|
| 62 | SDFGKITGKYCECDD | 511-525 |
| 63 | CECDDFSCVRYKGEM | 521-535 |
| 64 | YKGEMCSGHGQCSCG | 531-545 |
| 65 | QCSCGDCLCDSDWTG | 541-555 |
| 66 | SDWTGYYCNCTTRTD | 551-565 |
| 67 | TTRTDTCMSSNGLLC | 561-575 |
| 68 | NGLLCSGRGKCECGS | 571-585 |
| 69 | CECGSCVCIQPGSYG | 581-595 |
| 70 | PGSYGDTCEKCPTCP | 591-605 |
| 71 | CPTCPDACTFKKECV | 601-615 |
| 72 | KKECVECKKFDRGAL | 611-625 |
| 73 | DRGALHDENTCNRYC | 621-635 |
| 74 | CNRYCRDEIESVKEL | 631-645 |
| 75 | SVKELKDTGKDAVNC | 641-655 |
| 76 | DAVNCTYKNEDDCVV | 651-665 |
| 77 | DDCVVRFQYYEDSSG | 661-675 |
| 78 | EDSSGKSILYVVEEP | 671-685 |
| 79 | VVEEPECPKGPDILV | 681-695 |
| 80 | PDILVVLLSVMGAIL | 691-705 |
| 81 | MGAILLIGLAALLIW | 701-715 |
| 82 | ALLIWKLLITIHDRK | 711-725 |
| 83 | IHDRKEFAKFEEERA | 721-735 |
| 84 | EEERARAKWDTANNP | 731-745 |
| 85 | TANNPLYKEATSTFT | 741-755 |
| 86 | KEATSTFTNITYRGT | 748-762 |

TABLE 3

Summary of GPIIIa peptides eliciting PBMC proliferation from AITP patients in vitro

| AITP Patients | Platelet Count × 10⁹/L [at Testing] | HLA-DR Type DRB1* | HLA-DQ Type DQB1* | Anti-GPIIb/IIIa Status | | Stimulatory Peptides (SI > 3) Immunodominant Peptides in Bold |
|---|---|---|---|---|---|---|
| | | | | Serum | Eluate | |
| AITP1 | 10 | 03/11 | 02/03 | Pos | wPos | 2, 3, 44, 53, 68, 81, 82 |
| AITP2 | 102 | 07/11 | 02/03 | Pos | wPos | 42, 49, 50, 58, 60, 67, 70, 71, 72, 73, 74, 77, 78, 80, 81 |
| AITP3 | 3 | 01/01 | 05/05 | Pos | Pos | 2, 44, 50, 80, 82 |
| AITP4 | 14 | 01/04 | 03/05 | Neg | NT | 72, 82 |
| AITP5 | 163 | 03/04 | 02/03 | Neg | Pos | 82 |
| AITP6 | 33 | 03/07 | 02/03 | Neg | NT | None |
| AITP7 | 3 | 03/03 | 02/02 | Pos | Pos | 8, 11, 14, 15, 35, 40, 47, 56, 70, 82 |
| AITP8 | 16 | 03/07 | 02/02 | Neg | NT | 29, 34, 35, 36, 40, 44, 53, 77, 78, 80, 81 |
| AITP9 | 338 | 15/15 | 06/06 | Neg | Pos | 2, 6, 7, 14, 15, 30, 46, 47, 53, 82 |
| AITP10 | 394 | 01/03 | 02/05 | Pos | wPos | 2, 3, 44, 47, 53, 82 |
| AITP11 | 177 | 04/13 | 03/06 | Pos | Pos | 2, 32, 47, 53, 77, 82, 86 |
| AITP12 | 170 | 03/04 | 02/03 | Pos | Pos | 9, 17, 31, 53, 81, 82 |
| AITP13 | 127 | NT | NT | Pos | Neg | 69 |
| AITP14 | 49 | NT | NT | Neg | Pos | 54, 83 |
| AITP15 | 60 | 11/13 | 03/06 | Pos | Neg | 70 |

TABLE 3-continued

Summary of GPIIIa peptides eliciting PBMC proliferation from AITP patients in vitro

| AITP Patients | Platelet Count × 10⁹/L [at Testing] | HLA-DR Type DRB1* | HLA-DQ Type DQB1* | Anti-GPIIb/IIIa Status Serum | Anti-GPIIb/IIIa Status Eluate | Stimulatory Peptides (SI > 3) Immunodominant Peptides in Bold |
|---|---|---|---|---|---|---|
| AITP16 | 104 | 11/15 | 06/06 | Pos | Pos | 3, 47, 68, 74, 77, 82 |
| AITP17 | 163 | 01/03 | 02/05 | Neg | wPos | None |
| AITP18 | 62 | 13/13 | 03/06 | Pos | NT | 2, 44, 53, 82 |
| AITP19 | 152 | 15/15 | 06/06 | Pos | Pos | 2, 47, 48, 52, 82 |
| AITP20 | 61 | 04/15 | 03/06 | Pos | Pos | 2, 47, 50, 53, 70, 82 |
| AITP21 | 7 | 0103/15 | 05/06 | Pos | Pos | 1, 2, 29, 34, 44, 47, 49, 81, 82 |
| AITP22 | 76 | 15/15 | 06/06 | Neg | Pos | 2, 47, 53, 77, 82 |
| AITP23 | 5 | 07/15 | 02/06 | Pos | Pos | 5, 30, 31, 36, 47, 54, 60, 61, 86 |
| AITP24 | 163 | 01/07 | 03/03 | Pos | wPos | 2, 3, 44, 47, 53, 56, 70, 82 |
| AITP25 | 76 | NT | NT | Pos | Neg | 82 |
| AITP26 | NT | NT | NT | Neg | Pos | 2, 47, 53, 62, 63 |
| AITP27 | 95 | NT | NT | Pos | Neg | None |
| AITP28 | 260 | NT | NT | Pos | Neg | 4, 7, 9, 11, 21, 23, 24, 43, 57, 63, 69, 70 |
| AITP29 | 217 | NT | NT | Pos | Pos | 5, 9, 17, 32, 33, 36, 38, 40, 52, 53, 57, 70 |
| AITP30 | 121 | NT | NT | Neg | Neg | 2, 20, 41, 44, 47, 53, 76 |
| AITP31 | 327 | NT | NT | Pos | Neg | 2, 37, 47, 65, 82 |

NT = Not Tested; Pos = Positive Reaction; wPos = Weak Positive Reaction; Neg = Negative Reaction; SI = Stimulation Index

TABLE 4A

Summary of GPIIIa peptides eliciting PBMC proliferation from healthy controls in vitro

| Control Donors | HLA-DR Type DRB1* | HLA-DQ Type DQB1* | Anti-GPIIb/IIIa Status Serum | Anti-GPIIb/IIIa Status Eluate | Stimulatory Peptides (SI > 3) Immunodominant Peptides in Bold |
|---|---|---|---|---|---|
| C1 | 04/07 | 02/03 | NT | NT | None |
| C2 | 01/11 | 03/05 | Neg | Neg | None |
| C3 | 04/15 | 03/06 | Neg | Neg | None |
| C4 | 04/1325 | 02/02 | Neg | Neg | None |
| C5 | 13/15 | 06/06 | Neg | Neg | None |
| C6 | 07/11 | 02/02 | Neg | Neg | None |
| C7 | 03/15 | 02/06 | Neg | Neg | 75, 82 |
| C8 | 01/15 | 05/06 | NT | NT | 85 |
| C9 | 07/15 | 02/06 | Neg | Neg | None |
| C10 | 15/15 | 06/06 | Neg | Neg | None |
| C11 | 04/15 | 03/06 | Neg | Neg | 72 |
| C12 | 08/15 | 04/06 | Neg | Neg | 55, 82 |
| C13 | 03/03 | 02/02 | NT | NT | 12 |
| C14 | 04/07 | 03/03 | NT | NT | 82 |
| C15 | 13/15 | 03/06 | Neg | Neg | 11 |
| C16 | 07/15 | 02/06 | Neg | Neg | None |
| C17 | 04/13 | 03/06 | Neg | Neg | None |
| C18 | 01/04 | 03/05 | Neg | Neg | None |
| C19 | 03/11 | 02/03 | Neg | Neg | None |
| C20 | 01/14 | 05/05 | Neg | Neg | None |
| C21 | 03/03 | 0201/0202 | Neg | Neg | None |
| C22 | 01/03 | 02/05 | Neg | NT | 60 |
| C23 | 03/15 | 02/06 | Neg | Neg | None |
| C24 | 04/07 | 02/03 | Neg | Neg | 45, 73 |
| C25 | 15/15 | 06/06 | Neg | Neg | None |

NT = Not Tested; Neg = Negative Reaction; SI = Stimulation Index

TABLE 4B

Summary of GPIIIa peptides eliciting PBMC proliferation from disease control donors in vitro

| Patient Controls | Sex | Age [at testing] [years] | Clinical Disease | Platelet Count [at testing] | Stimulatory peptides (SI > 3) Immunodominant Peptides in Bold |
|---|---|---|---|---|---|
| C26 | M | 54 | Aplastic anemia | 4 | None |
| C27 | M | 56 | Aplastic anemia | 49 | None |

TABLE 4B-continued

Summary of GPIIIa peptides eliciting PBMC proliferation from disease control donors in vitro

| Patient Controls | Sex | Age [at testing] [years] | Clinical Disease | Platelet Count [at testing] | Stimulatory peptides (SI > 3) Immunodominant Peptides in Bold |
|---|---|---|---|---|---|
| C28 | M | 64 | Aplastic anemia | 3 | None |
| C29 | M | 24 | Aplastic anemia | 4 | 14 |
| C30 | F | 69 | Aplastic anemia | 23 | 82 |

TABLE 5

Summary of predicted motifs in dominant GPIIIa peptides for binding to HLA-DR molecules and responsiveness of PBMC from AITP patients

| Dominant Peptide Number | Position on GPIIIa@ | HLA-DR molecules Bound with High Affinity+ | AITP Patients with PBMC Response to Peptide — High Affinity DR Expressed | AITP Patients with PBMC Response to Peptide — No High Affinity DR Expressed |
|---|---|---|---|---|
| 2 (aa6-20) | PSI domain | None | None | AITP1, AITP3, AITP9, AITP10, AITP11, AITP18, AITP19, AITP20, AITP21, AITP22, AITP24 |
| 44 (aa331-345) | Spanning bA and hybrid domain | DR04, DR07 | AITP8, AITP24 | AITP1, AITP3, AITP10, AITP18, AITP21 |
| 47 (aa361-375) | Hybrid domain | None | None | AITP7, AITP9, AITP10, AITP11, AITP16, AITP19, AITP20, AITP21, AITP22, AITP23, AITP24, AITP26 |
| 53 (aa421-435) | Spanning hybrid and PSI domain | DR04, DR13 | AITP11, AITP-12, AITP18, AITP20 | AITP1, AITP8, AITP9, AITP10, AITP22, AITP24 |
| 70 (aa591-605) | EGF-like domain | None | None | AITP2, AITP7, AITP15, AITP20, AITP24 |
| 77 (aa661-675) | EGF-like domain | DR04, DR15 | AITP11, AITP16, AITP22 | AITP2, AITP8 |
| 82 (aa711-725) | bTD domain (Trans-membrane/ cytoplasmic) | DR01, DR08, DR11, DR13, DR15 | *AITP1, AITP3, AITP4, AITP5, AITP9, AITP10, AITP11, AITP16, AITP18, AITP19, AITP20, AITP21, AITP22, AITP24 | *AITP7, AITP12 |

@From structural analysis of b3 integrin
+Predicted using the Propred algorithm (www.imtech.res.in/raghava/propred)
*Significant association between response to peptide 82 and expression of HLA-DR molecules to which peptide predicted to bind with high affinity ($\chi^2 = 10$; $p < 0.05$)

The invention claimed is:

1. A method of treating a disease associated with autoantibodies specific for platelet proteins, the method comprising administering to a patient an epitope of the platelet protein, wherein the epitope is selected from the group consisting of SEQ ID No: 2, 44, 47, 53, 70, 77 and 82.

2. The method of claim 1 wherein the disease is autoimmune thrombocytopenic purpura.

3. The method of claim 1 wherein the composition is formulated for delivery through non-invasive routes or invasive routes.

4. The method of claim 1 wherein the composition is formulated for delivery through mucosal tissue.

5. The method of claim 1 wherein the epitope is selected from the group consisting of SEQ ID No: 2, 47, 53 and 82.

* * * * *